US011219411B2

(12) United States Patent
Iskander et al.

(10) Patent No.: US 11,219,411 B2
(45) Date of Patent: *Jan. 11, 2022

(54) LUNG WATER CONTENT MEASUREMENT SYSTEM AND CALIBRATION METHOD

(71) Applicant: University of Hawaii, Honolulu, HI (US)

(72) Inventors: Magdy F. Iskander, Honolulu, HI (US); Ruthsenne R. G. Perron, Waipahu, HI (US)

(73) Assignee: University of Hawaii, Honolulu, HI (US)

( * ) Notice: Subject to any disclaimer, the term of this patent is extended or adjusted under 35 U.S.C. 154(b) by 1368 days.

This patent is subject to a terminal disclaimer.

(21) Appl. No.: 15/042,109

(22) Filed: Feb. 11, 2016

(65) Prior Publication Data
US 2016/0310072 A1    Oct. 27, 2016

Related U.S. Application Data

(60) Provisional application No. 62/196,871, filed on Jul. 24, 2015, provisional application No. 62/115,549, filed on Feb. 12, 2015.

(51) Int. Cl.
*A61B 5/0507* (2021.01)
*A61B 5/08* (2006.01)
(Continued)

(52) U.S. Cl.
CPC .......... *A61B 5/4878* (2013.01); *A61B 5/0507* (2013.01); *A61B 5/08* (2013.01);
(Continued)

(58) Field of Classification Search
CPC ............ A61B 5/0507; A61B 5/08–097; A61B 5/6823; A61B 5/4878
See application file for complete search history.

(56) References Cited

U.S. PATENT DOCUMENTS

| 4,240,445 A | 12/1980 | Iskander et al. |
| 4,488,559 A | 12/1984 | Iskander |
(Continued)

FOREIGN PATENT DOCUMENTS

| CN | 85107022 A | 4/1987 |
| GB | 2500000 A | 9/2013 |
(Continued)

OTHER PUBLICATIONS

Iskander et al. "Diagnosis of pulmonary edema by a surgically noninvasive microwave technique." Radio Science vol. 14, No. 65, pp. 265-269, Nov.-Dec. 1979. (Year: 1979).*
Iskander et al. "A microwave method for measuring changes in lung water content: numberical simulation." IEEE transactions on BME, vol. BME-28, No. 12, pp. 797-804, Dec. 1981. (Year: 1981).*
(Continued)

*Primary Examiner* — Angela M Hoffa
(74) *Attorney, Agent, or Firm* — Knobbe, Martens, Olson & Bear, LLP

(57) ABSTRACT

A system and method for monitoring lung water content of a patient. The system may include microwave sensors and a processor. The system may transmit microwave signals into, and receive microwave signals from, the thorax of a patient using the microwave sensors. The received microwave signals may each have at least one frequency component with a magnitude and a phase. The system may analyze the phase of the received microwave signal corresponding to a first pair of the microwave signals to monitor changes in the lung water content. The system may analyze the magnitude of the received microwave signal corresponding to a second, different pair of the microwave sensors to determine whether the lung water content is increasing or decreasing. The system may also analyze the received microwave signals to determine a blood pressure indicator and to determine lung water content.

19 Claims, 22 Drawing Sheets

(51) Int. Cl.
    *A61B 5/00*     (2006.01)
    *G16H 40/63*     (2018.01)
    *A61B 5/029*     (2006.01)
    *A61B 5/024*     (2006.01)
    *A61B 5/0205*     (2006.01)
    *A61B 5/021*     (2006.01)

(52) U.S. Cl.
    CPC .......... *A61B 5/6823* (2013.01); *A61B 5/7246* (2013.01); *A61B 5/7275* (2013.01); *A61B 5/7278* (2013.01); *A61B 5/7282* (2013.01); *A61B 5/00* (2013.01); *A61B 5/021* (2013.01); *A61B 5/024* (2013.01); *A61B 5/0205* (2013.01); *A61B 5/029* (2013.01); *A61B 5/0809* (2013.01); *A61B 5/0816* (2013.01); *A61B 2560/0223* (2013.01); *A61B 2562/0228* (2013.01); *G16H 40/63* (2018.01)

(56) References Cited

U.S. PATENT DOCUMENTS

| | | | |
|---|---|---|---|
| 4,510,437 | A | 4/1985 | Alden et al. |
| 5,045,862 | A | 9/1991 | Alden et al. |
| 5,749,369 | A | 5/1998 | Rabinovich et al. |
| 7,149,576 | B1 | 12/2006 | Baura et al. |
| 7,591,792 | B2* | 9/2009 | Bouton ..................... A61B 5/05 343/718 |
| 7,811,234 | B2 | 10/2010 | McGrath |
| 8,989,837 | B2* | 3/2015 | Weinstein ............ A61B 5/0507 600/407 |
| 9,002,427 | B2* | 4/2015 | Tupin, Jr ............. A61B 5/0507 600/407 |
| 9,265,438 | B2* | 2/2016 | Weinstein ............ A61B 5/6823 |
| 9,526,438 | B2* | 12/2016 | Iskander ............. A61B 5/6804 |
| 9,572,512 | B2* | 2/2017 | Weinstein ............ A61B 5/0507 |
| 10,307,102 | B2* | 6/2019 | Saroka ................. A61B 5/6844 |
| 10,588,599 | B2* | 3/2020 | Weinstein .......... A61N 1/36578 |
| 10,856,806 | B2* | 12/2020 | Iskander ............. A61B 5/6823 |
| 2002/0071570 | A1 | 6/2002 | Cohen et al. |
| 2004/0249298 | A1 | 12/2004 | Selevan |
| 2005/0235482 | A1 | 10/2005 | Deaett et al. |
| 2006/0220961 | A1 | 10/2006 | Tinsley et al. |
| 2006/0247505 | A1 | 11/2006 | Siddiqui |
| 2006/0259027 | A1 | 11/2006 | Kwan et al. |
| 2008/0234574 | A1 | 9/2008 | Hancock et al. |
| 2010/0022900 | A1 | 1/2010 | Peterson |
| 2010/0256462 | A1 | 10/2010 | Rappaport et al. |
| 2011/0060215 | A1* | 3/2011 | Tupin, Jr ............... A61B 5/091 600/425 |
| 2011/0130800 | A1* | 6/2011 | Weinstein ............ A61B 5/0507 607/17 |
| 2011/0237939 | A1 | 9/2011 | Malemed et al. |
| 2011/0306859 | A1 | 12/2011 | Saldivar et al. |
| 2013/0187666 | A1 | 7/2013 | Rubinsky et al. |
| 2014/0012149 | A1 | 1/2014 | Trice |
| 2014/0323823 | A1 | 10/2014 | Iskander et al. |
| 2014/0323893 | A1 | 10/2014 | Ghosh et al. |
| 2015/0208949 | A1* | 7/2015 | Tupin, Jr ............. A61B 5/6831 600/407 |
| 2016/0150959 | A1* | 6/2016 | Mizrahi ................ A61B 5/721 600/430 |
| 2016/0235331 | A1* | 8/2016 | Iskander ............. A61B 5/7282 |
| 2016/0345845 | A1 | 12/2016 | Ravid et al. |
| 2017/0258366 | A1* | 9/2017 | Tupin, Jr ............. A61B 5/0803 |

FOREIGN PATENT DOCUMENTS

| | | |
|---|---|---|
| JP | 2007-509353 A | 4/2007 |
| WO | WO 2009/031149 A2 | 3/2009 |

OTHER PUBLICATIONS

Gagarin et al, "determination of pulmonary edema using microwave sensor array: simulation studies with anatomically realistic human CAD-models." IEEE, pp. 2189-2190, 2013. (Year: 2013).*

Rezaeieh et al, "microwave system for the early stage detection of congestive heart failure." IEEE Access, vol. 2, pp. 921-929, Jan. 2014. (Year: 2014).*

Gagarin et al, "microwave stethoscope: a new method for measuring human vital signs." IEEE pp. 404-407, 2011. (Year: 2011).*

Celik et al., "Microwave Stethoscope (MiSt) as a Low-Cost Vital Signs Sensor: Results from Preliminary Human Subject Stufies", Hawaii Center for Advanced Communications, University of Hawaii at Manoa, 2012 in 4 pages.

Celik et al., "On the Development of a Low-Cost Real-Time Remote Patient Monitoring System using a Novel Non-invasive Microwave Vital Signs Sensor." Hawaii Center for Adv. Communications, University of Hawaii, 2010 in 4 pages.

Celik, et al., "A Non-Invasive microwave sensor and signal processing technique for continuous monitoring of vital signs," IEEE Antennas and Wireless Propagation Letters, vol. 10, pp. 286-289, Feb. 2011.

Celik et al., Microwave stethoscope: Development and benchmarking of a vital signs sensor using computer-controlled phantoms and humans studies. IEEE transactions on Biomedical Engineering, 61(8), 2341-2349. (Year: 2013).

Extended European Search Report issued in application No. 15782448.3 dated Nov. 16, 2017.

Gagarin et al., "Determination of Pulmonary Edema Using Microwave Sensor Array: Simulation Studies With Anatomically Realistic Human CAD-Models", Hawaii Center for Advanced Communications, College of Engineering, University of Hawaii, 2013 pp. 2189-2190.

Gagarin et al., "Microwave Stethoscope, A New Noninvasive Multiple Vital Signs Sensor: Human Clinical Trials", Hawaii Center for Advanced Communications College of Engineering, University of Hawaii, 2012 in 2 pages.

Gagarin et al., "Noninvasive Microwave Technique for Hemodynamic Assessments", Hawaii Center for Advanced Communcations, University of Hawaii, 2010 in 4 pages.

Gagarin et al., "Textile Sensor for Monitoring Vital Signs", Hawaii Center for Advanced Communications, College of Engineering, University of Hawaii, 2014 in 2 pages.

Gagarin, et al., "Microwave Stethoscope: a new method for measuring human vital signs," Antennas and Propagation (APS-URSI International Conference), IEEE International Symposium, Jul. 2011.

International Search Report and Written Opinion issued in application No. PCT/US2015/027628 dated Jul. 24, 2015.

Iskander, et al., "A microwave method for estimating absolute value of average lung water," Radio Science, vol. 17, p. 111, 1982.

Iskander, et al., "Microwave Methods of Measuring Changes in Lung Water," Journal of Microwave Power, vol. 18, pp. 265-275, 1983.

Iskander, et al., "Diagnosis of pulmonary edema by a surgically non-invasive microwave technique," Radio Science, vol. 14, pp. 265-269, 1979.

Office Action issued in Japanese application No. 2016-564187 dated Mar. 12, 2019.

Perron et al., "Dynamic 3D Model of Human Thorax for the Assessment of Changes in Lung Fluid Content and Vital Signs", Hawai'i Center for Advanced Communications College of Engineering, University of Hawai'I, 2016 in 2 pages.

Perron et al., "Multi-Sensor Cardio-Pulmonary Stethoscope for Quantitative Lung Water Measurement", 32nd URSI GASS, Montreal, Aug. 19-26, 2017.

Tamaye et al., "CP-Stethoscope: Phantom Model Experiments", Hawai'i Center for Advanced Communications, College of Engineering, University of Hawaii, 2016, in 2 pages.

Yun, et al., "Extraction of Lung Water Content from Computerized Tomography Scans", Hawaii Advanced Wireless Technologies Institute, University of Hawaii at Manoa, 2019 pp. 531-532.

Yun et al., "Mapping Lung Water Signal Distribution on Human Chest and Predition of Lung Water Content", Hawaii Advanced Wireless Technologies Institute, 2019 pp. 751-752.

(56) References Cited

OTHER PUBLICATIONS

Salman, et al., (2014). Pulmonary edema monitoring sernsor with integrated body-area network for remote medical sensing. IEEE transactions on Antennas and Propagation, 62(5), 2787-2794. (Year: 2014).

Lin, J. C. (1986). Microwave propagation in biological dielectrics with application to cardiopulmonary interrogation. Medical applications of microwave imaging, 47-58. (Year: 1986).

Iskander, et al. (1981). A microwave method for measuring changes in lung water content numerical simulation. IEEE Transactions on Biomedical Engineering, (12), 797-804. (Year: 1981).

\* cited by examiner

| (S,S) | 1 | | 2 | | 3 | | 4 | | 5 | | 6 | | 7 | | 8 | | 9 | | 10 | |
|---|---|---|---|---|---|---|---|---|---|---|---|---|---|---|---|---|---|---|---|---|
| Δ | Mag | Pha | Mag | Pha | Mag | Pha | Mag | Pha | Mag | Pha | Mag | Pha | Mag | Pha | Mag | Pha | Mag | Pha | Mag | Pha |
| 1 | -0.14 | -1.4 | 8.23 | -16.7 | -9.97 | -56.8 | 3.52 | -71.3 | -14.53 | -253.4 | 13.42 | -75.5 | -14.75 | -96.7 | 18.77 | -138.8 | -2.36 | -58.4 | -0.65 | -15.5 |
| 2 | 8.23 | -16.7 | 0.13 | 0.7 | 9.28 | 28 | -7.24 | 4.4 | -3.88 | -41 | 13.29 | -227.3 | 11.71 | -273.8 | 7.3 | -318.7 | -4.72 | 7.5 | 3.91 | -52 |
| 3 | -9.97 | -56.8 | 9.28 | 28 | 0.16 | -1.2 | -5.89 | 44.1 | 8.45 | -84.7 | -8.15 | 26.7 | 11.67 | -250.6 | -6.86 | -288.9 | -0.56 | -4.2 | -4.62 | 18.8 |
| 4 | 3.52 | -71.3 | -7.24 | 4.4 | -5.89 | 44.1 | 0.14 | 0.7 | 2.55 | 14.8 | -5.66 | -20.1 | -3.79 | -46.7 | -5.16 | -159.6 | -5.42 | -10.3 | -6.3 | 7.8 |
| 5 | -14.53 | -253.4 | -3.88 | -41 | 8.45 | -84.7 | 2.55 | 14.8 | -0.16 | -0.9 | -0.88 | -6.2 | -2.56 | 45.8 | -1.54 | -33.8 | -3.88 | -58.9 | -1.46 | -40.7 |
| 6 | 13.42 | -75.5 | 13.29 | -227.3 | -8.15 | 26.7 | -5.66 | -20.1 | -0.88 | -6.2 | 0.09 | -1.1 | -0.95 | 3.2 | -2.43 | 43.4 | 11.33 | -187.1 | -20.31 | -91.4 |
| 7 | -14.75 | -96.7 | 11.71 | -273.8 | 11.67 | -250.6 | -3.79 | -46.7 | -2.56 | 45.8 | -0.95 | -1.1 | 0.1 | 1.1 | -0.33 | -6.3 | 1.84 | -32.1 | -6.54 | 38.9 |
| 8 | 18.77 | -138.8 | 7.3 | -318.7 | -6.86 | -288.9 | -5.16 | -159.6 | -1.54 | -33.8 | -2.43 | 43.4 | -0.33 | -6.3 | -0.13 | 1.5 | 3.91 | 29.5 | -8.13 | 53.9 |
| 9 | -2.36 | -58.4 | -4.72 | 7.5 | -0.56 | -4.2 | -5.42 | -10.3 | -3.88 | -58.9 | 11.33 | -187.1 | 1.84 | -32.1 | 3.91 | 29.5 | 0.18 | 1.8 | 2.26 | -17.1 |
| 10 | -0.65 | -15.5 | 3.91 | -52 | -4.62 | 18.8 | -6.3 | 7.8 | -1.46 | -40.7 | -20.31 | -91.4 | -6.54 | 38.9 | -8.13 | 53.9 | 2.26 | -17.1 | 0.09 | 0.4 |

FIG. 16

LUNG WATER CONTENT MEASUREMENT SYSTEM AND CALIBRATION METHOD

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. In particular, this application claims priority to U.S. Provisional Patent Application 62/115,549, filed Feb. 12, 2015, and entitled "Multi-Sensor and Automated Segmented Calibration Method," and to U.S. Provisional Patent Application 62/196,871, filed Jul. 24, 2015, and entitled "LUNG WATER CONTENT MEASUREMENT SYSTEM AND CALIBRATION METHOD," both of which are hereby incorporated by reference in their entireties.

STATEMENT REGARDING FEDERALLY SPONSORED R&D

This invention was made with government support under Grant No. R21 HL124457 awarded by the National Institutes of Health, and under Grant Nos. IIP1127956 and OISE1059673 awarded by the National Science Foundation. The government has certain rights in the invention.

BACKGROUND

Field

This disclosure relates to a non-invasive microwave instrument with an array of microwave sensors. The microwave system can be used for collecting, analyzing, and displaying physiological information.

Description of the Related Art

Improving healthcare is one of the most pressing challenges facing the world in the 21st century. In order to meet this challenge, there is a need for patient monitoring systems to track a variety of vital signs (VS), including lung water content (LWC). LWC is a medically-important parameter because it can be used, for example, to reliably detect heart failure and pulmonary edema at early stages.

SUMMARY

In some embodiments, a method of monitoring lung water content of a patient using at least two microwave sensors comprises: transmitting one or more microwave signals into the thorax of a patient using one or more microwave sensors; receiving one or more of the microwave signals using one or more microwave sensors, the one or more received microwave signals each comprising at least one frequency component having a magnitude and a phase; analyzing the phase of one or more received microwave signals to monitor changes in the lung water content; and analyzing the magnitude of one or more received microwave signals to determine whether the lung water content is increasing or decreasing.

In some embodiments, a system for monitoring a physiological characteristic of a patient comprises: more than two microwave sensors; and a processor configured to perform a method comprising measuring microwave scattering parameters from the microwave sensors, the microwave scattering parameters comprising at least microwave transmission coefficients respectively corresponding to a selected first microwave sensor and at least a second microwave sensor and a third microwave sensor; analyzing the measured microwave transmission coefficients to determine the physiological characteristic.

In some embodiments, a system for monitoring lung water content of a patient comprises: at least two microwave sensors; and a processor configured to perform a method comprising transmitting one or more microwave signals into the thorax of a patient using one or more of the microwave sensors; receiving a first waveform corresponding to a first pair of the microwave sensors; analyzing at least one characteristic of the first waveform to determine a physiological characteristic.

BRIEF DESCRIPTION OF THE DRAWINGS

FIG. 16 is a chart of the magnitude and phase of the complete set of scattering parameters for a monitoring system which includes an array of microwave sensors.

DETAILED DESCRIPTION

Certain preferred embodiments of a microwave medical monitoring instrument are described in detail below. The instrument monitors physiological information by transmitting microwaves into a patient's thorax using microwave sensors, and then measuring microwave scattering parameters, also using microwave sensors. The instrument is an integrated, multipurpose low-cost and non-invasive system, with multiple microwave sensors, which can be used for conveniently monitoring the patient condition (e.g., on a mobile device). The system is designed and equipped with digital signal processing algorithms for making multiple vital sign (VS) measurements, including lung water content (LWC), respiration rate (RR), respiration amplitude (RA), heart rate (HR), heart-beat amplitude (HA), stroke volume (SV), cardiac output (CO), and others. Some aspects of the microwave medical monitoring instrument are described in U.S. patent application Ser. No. 14/261,884, filed Apr. 25, 2014, and entitled "MICROWAVE STETHOSCOPE FOR MEASURING CARDIO-PULMONARY VITAL SIGNS AND LUNG WATER CONTENT," which is hereby incorporated by reference herein in its entirety.

Figure 1:
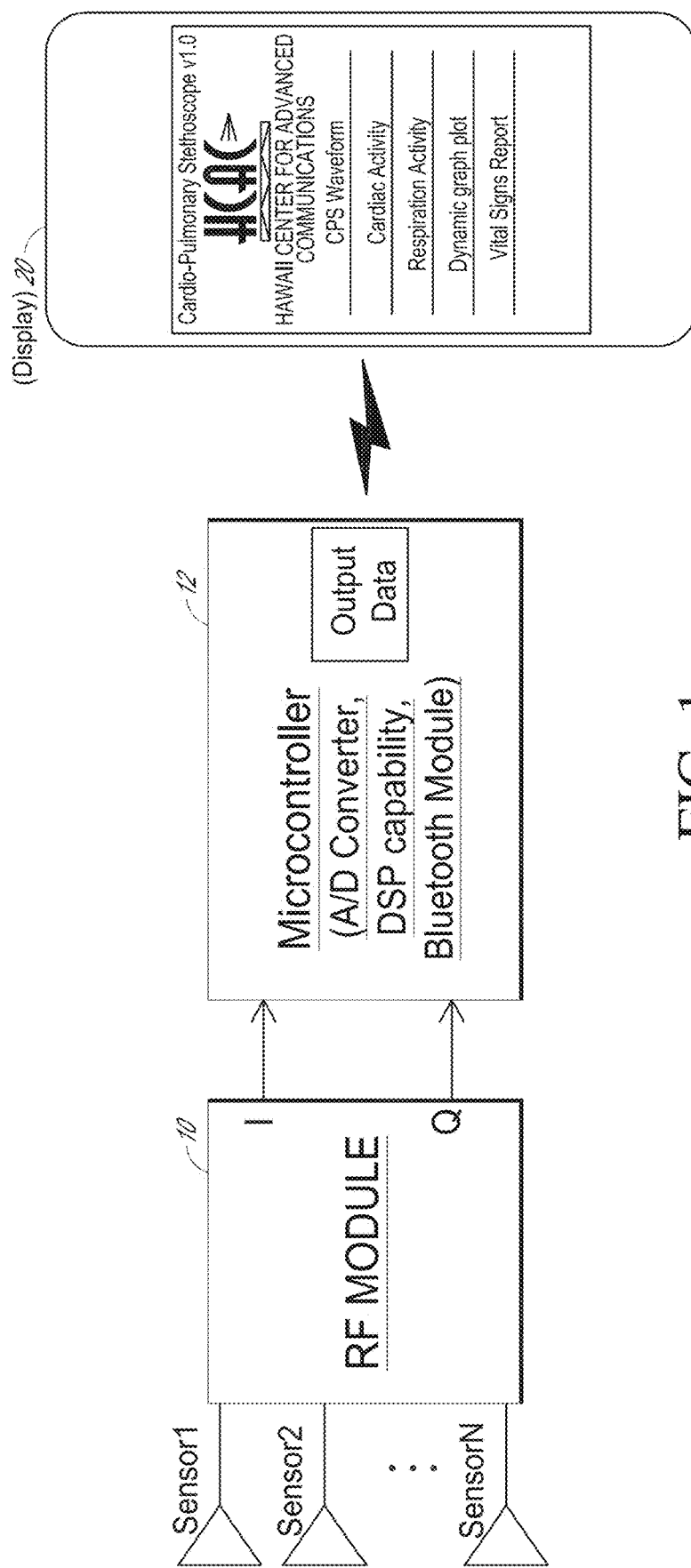
FIG. 1 is a schematic diagram illustrating a cardiopulmonary (CP) microwave stethoscope measurement method and device configuration.

By way of background, FIG. 1 is a schematic diagram which illustrates a cardio-pulmonary (CP) microwave stethoscope measurement method and device configuration employing a sensor array comprised of N microwave transmission/reception sensors placed on a patient's chest in spaced-apart configuration for taking integrated vital signs (VS) and lung water content (LWC) and other critical measurements. In some embodiments, the value of N is greater than two and depends upon the particular monitoring application for which the system is being used. Sensor-1, Sensor-2, and Sensor-N are microwave sensors which can couple microwaves into and out of the body. A radio-frequency (RF) module 10 is used to send a microwave signal to the transmission Sensor-1 which transmits the signal through the skin and tissues of the thorax in position at a patient heart-lung location, and receives a returned scattered microwave signal at the reception Sensor-2 and/or Sensor-N which is returned to the RF module 10. Conversely, Sensor-2 or Sensor-N can be used to transmit a signal through the skin and tissues of the thorax to Sensor-1.

The signal transmission and reception is controlled by a microcontroller 12 which may be incorporated with or in a separate unit from the RF module 10. The microcontroller 12 includes an analog-to-digital (A/D) signal converter, and digital signal processing (DSP) capability for analyzing the returned microwave signals and converting them to vital signs measurements. A wireless (e.g., Bluetooth) communication capability may be provided to send output data by wireless transmission to a display 20. For remote and/or home-based patient monitoring, the display 20 may be a smartphone display operated by a client display application (smartphone app).

Figure 2:
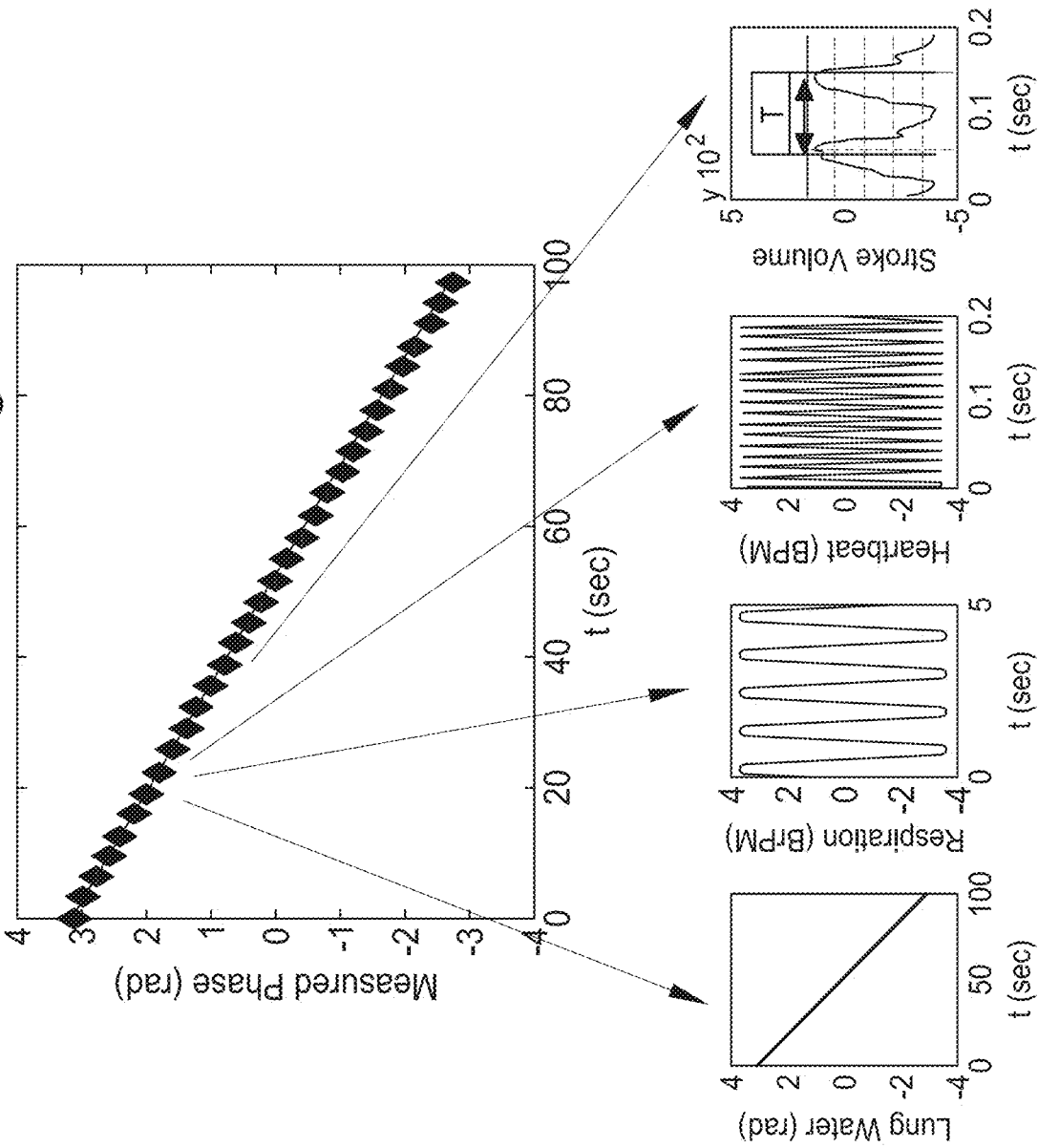
FIG. 2 illustrates conversion of the returned microwave measurement signal into various critical measurement displays provided by the system.

FIG. 2 illustrates conversion of the returned measurement signal into various clinical measurement displays provided by the system, such as Lung Water, Respiration (BrPM), Heartbeat (BPM), and Stroke Volume displays.

Figure 3:
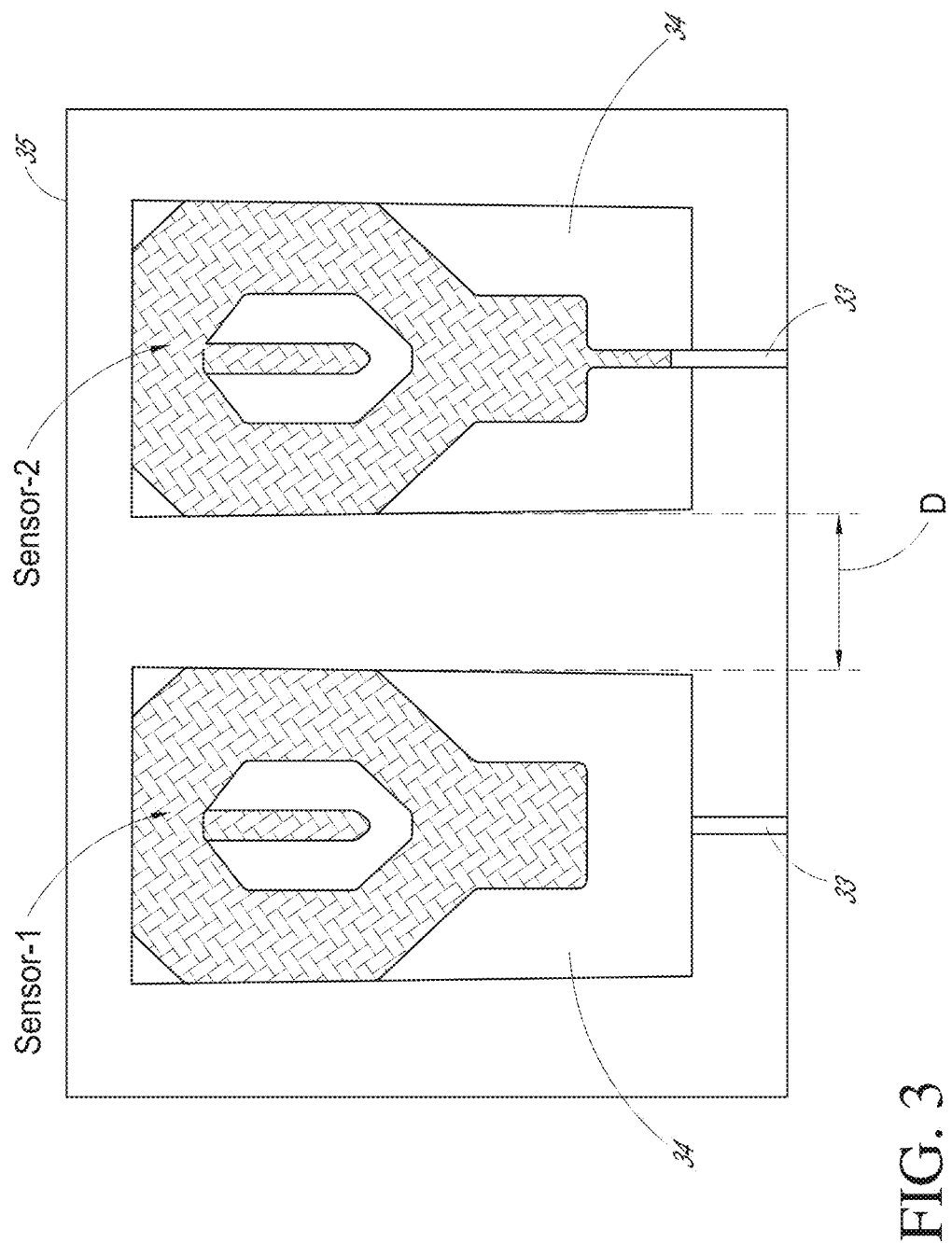
FIG. 3 shows the transmission Sensor-1 and reception Sensor-2 carried on a substrate in side-by-side configuration.

FIG. 3 shows a microwave transmission Sensor-1 and reception Sensor-2 embedded on patch substrates 34 in side-by-side configuration on a base layer 35 for mounting them on the skin on a patient's chest. As discussed herein, the base layer 35 can include additional microwave sensors arranged in an array. A preferred design for the microwave sensors is a coplanar waveguide structure with a center micro line strip in a central aperture that is carried on a substrate. The various microwave sensors may be of the same design or different designs. Two adjacent sensors are spaced apart by a spacing distance D, which is chosen to minimize or reduce electromagnetic (EM) coupling between the proximate conductive edges of the sensors and to maximize or increase signal-to-noise ratio (SNR) of the returned signal. In some embodiments, the separation distance D is about 1-3 cm. Larger separations may be found to result in weaker signals (low SNR) and closer separations may result in a strong electromagnetic (EM) coupling between the sensors and reduce sensitivity to vital signs and changes in lung water content.

Figure 4:
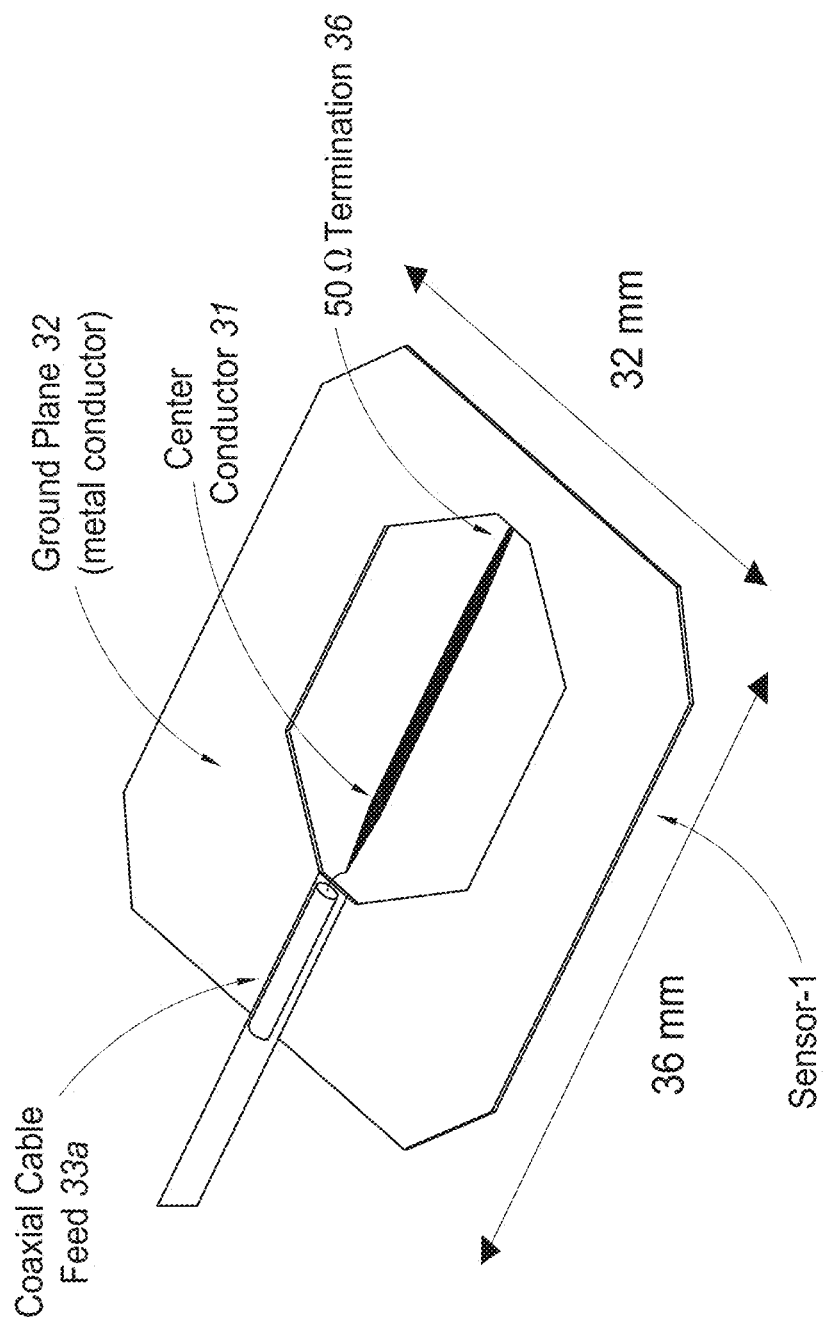
FIG. 4 shows a preferred example of the microwave transmission sensor with an adapter connector to a feeder coaxial cable.

FIG. 4 shows a preferred example for a microwave sensor having a coaxial cable feed line 33a connected to a microstrip center conductor 31 positioned in a central aperture of and terminating in a resistive (e.g. 50 ohm) termination 36 in electrical contact with a metal conductor ground plane 32. The sensor is shown with length-width dimensions of 34 mm×32 mm for illustration.

Figure 5:
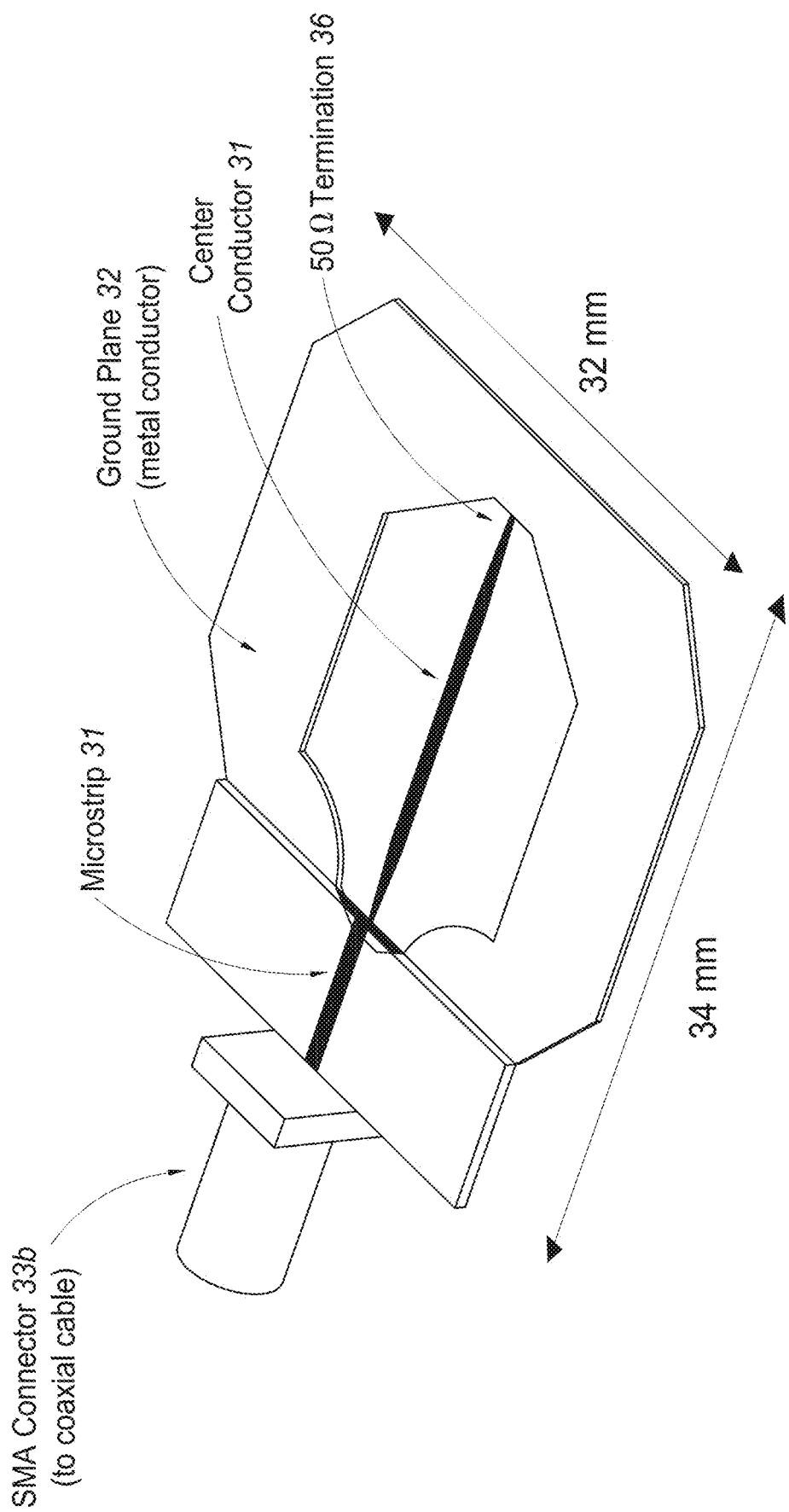
FIG. 5 shows an alternative structure for the microwave transmission sensor with a direct coaxial cable feeding structure.

FIG. 5 shows an alternative structure for a microwave sensor having an adapter (SMA) connector for a coaxial cable connection to the microstrip center conductor 31. The sensor is shown with length-width dimensions of 36 mm×32 mm for illustration.

Each microwave sensor can be designed so as to couple microwave radiation into the body of a patient in a localized region about the approximate footprint of the microwave sensor with relatively little leakage into the air or outside this footprint. Localized coupling of microwave radiation into a patient's body at the specific location of each microwave sensor helps reduce external signal leakage and mutual coupling of non-physiological information carrying signals amongst surrounding sensors. If a signal from a transmitting microwave sensor can propagate to a receiving microwave sensor without the transmitted energy first having interacted with the physiological structures or processes which are desired to be monitored, then the received energy will in general not be useful in providing physiological information about the patient but will instead tend to obscure signals which do carry physiological information. Localized coupling of microwave radiation into the body within the approximate footprint of each microwave sensor can be particularly important in embodiments which include arrays of several sensors, as described further herein. This is true because larger numbers of microwave sensors in the sensing array can potentially lead to increased opportunities for external leakage and undesired mutual coupling between microwave sensors.

In some embodiments, localized coupling of microwave energy into the body within the approximate footprint of each microwave sensor can be improved by designing each microwave sensor to exhibit impedance matching characteristics while in the as-worn measurement position proximate to the body of a patient (e.g., while the microwave sensor is in contact with skin, muscle, tissue, etc.). In other words, each microwave sensor can be designed so as to be substantially impedance matched with the feeding transmission line when coupled to the body of the patient rather than being substantially impedance matched to the feed line while located in free space without considering the effect of the patient's body on the impedance characteristics of the microwave sensor. In some embodiments, the feeding transmission line (e.g., the coaxial cable 33a) can have a characteristic impedance of, for example, 50Ω or 75Ω. In such embodiments, the microwave sensor can be designed to exhibit a substantially matched impedance when the sensor is coupled to the body of the patient.

Figure 6A:
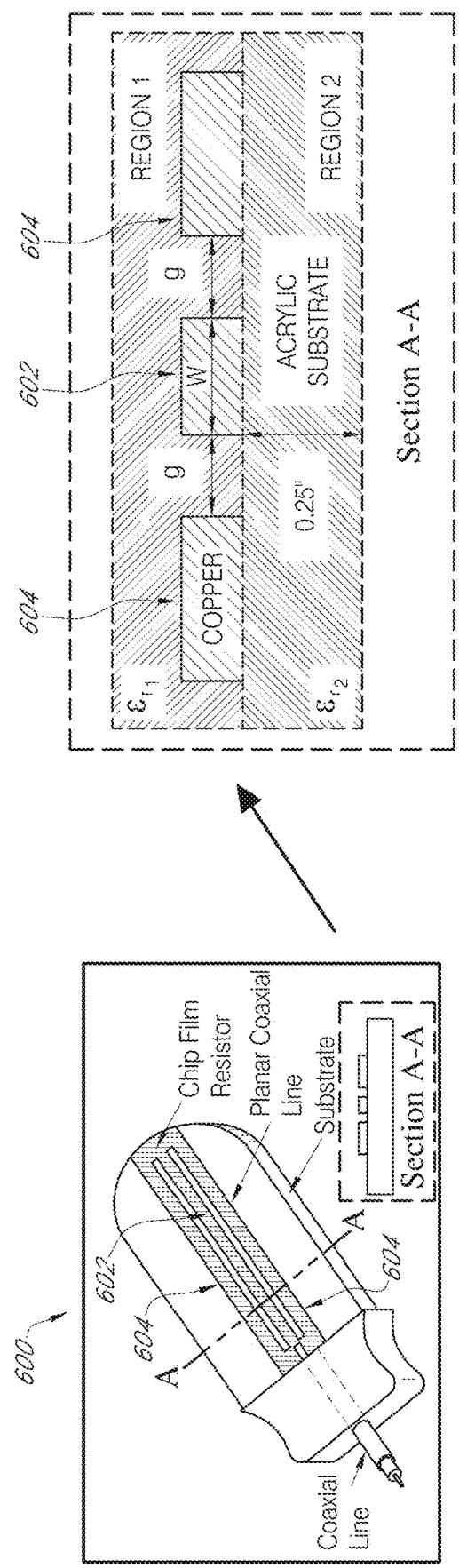
FIG. 6A is a schematic illustration of a model which can be used to design the impedance characteristics of a microwave sensor when it is coupled to the body of a patient.

FIG. 6A is a schematic illustration of a model which can be used to design the impedance characteristics of the microwave sensor 600 when it is coupled to the body of a patient. As discussed herein, in some embodiments the microwave sensor 600 can have a planar coaxial transmission line design having a center conductor 602 which spans an aperture formed in a coplanar ground plane 604. The central conductor 602 can be fed at one end by, for example, a coaxial line and can be terminated at the opposite end by a resistor.

Figure 6B:
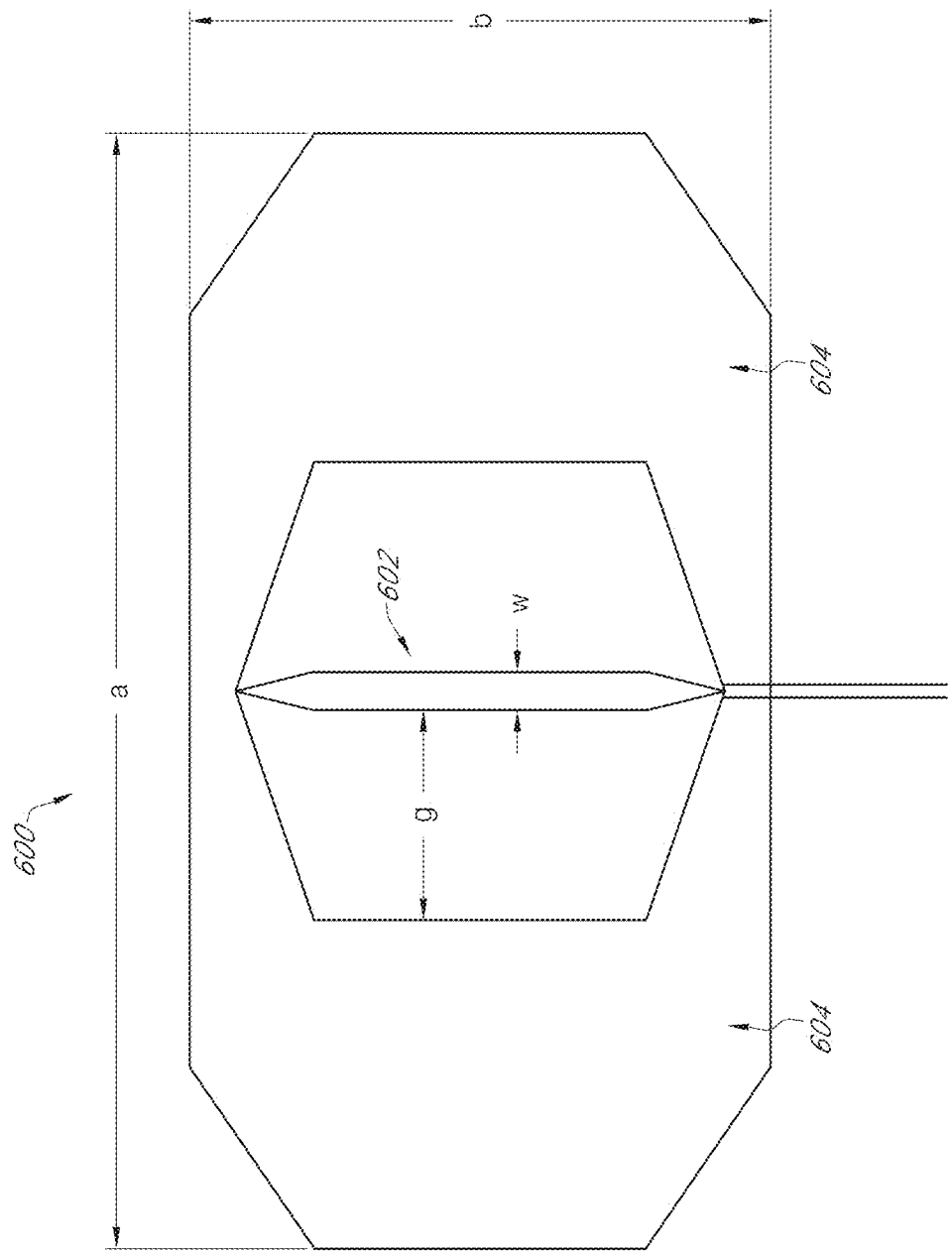
FIG. 6B shows a cross-sectional view through the microwave sensor at the line A-A in FIG. 6A.

FIG. 6B shows a cross-sectional view through the microwave sensor 600 at the line A-A. As shown in the cross-sectional view, the center conductor 602 and the coplanar ground plane 604 of the microwave sensor 600 can be modeled as a metal, such as copper. "Region 1" above the center conductor 602 and coplanar ground plane 604 of the microwave sensor 600 can be modeled as a substance having an electrical permittivity $\varepsilon_{r1}$. Meanwhile, "Region 2" below the microwave sensor can be modeled as a substance having an electrical permittivity $\varepsilon_{r2}$. In some embodiments, Region 1 represents air and Region 2 represents the body of a patient. (An intervening substrate layer can also be modeled between the conductors and Region 2.) Therefore, $\varepsilon_{r1}$ can be given the value of the permittivity of air whereas $\varepsilon_{r2}$ can be given the value of the permittivity of skin, muscle, or tissue. According to this model, the characteristic impedance $Z_0$ of the microwave sensor 600, in the as-worn position coupled with the body of the patient, can be calculated according to the following example equations:

$$Z_0 = (60\pi) \frac{K'}{K\sqrt{(\varepsilon_{r_1} + 1)(\varepsilon_{r_2} + 1)}}$$

$$k = \frac{w}{w + 2g}$$

$$k' = \sqrt{1 - k^2}$$

where K can be calculated from the complete elliptic integrals of k, K' can be calculated from the complete elliptic integrals of k', and where w is the width of the center conductor 602 and g is the gap between the center conductor 602 and the ground plane 604.

As already discussed, the characteristic impedance $Z_0$ of the microwave sensor 600 while in the as-worn position coupled with the body of the patient can be substantially matched to the characteristic impedance of the feed line. This results in reduced reflections and standing waves and, consequently, improved localized coupling of microwave energy into the body of the patient. FIG. 6B illustrates an example microwave sensor 600 with dimensions calculated so as to exhibit matched impedance characteristics with a 50Ω feed line while the microwave sensor 600 is coupled to the body of a patient. In the illustrated embodiment, the transverse dimension, a, of the microwave sensor 600 can be approximately 52.4 mm, while the longitudinal dimension, b, can be approximately 35.4 mm. The gap, g, between the center conductor 602 and the ground plane 604 can be approximately 9.9 mm, while the width, w, of the center conductor can be approximately 1.6 mm. It should be understood, however, that these dimensions merely represent an example embodiment and that many other embodiments are possible depending upon the specific application.

Figure 6C:
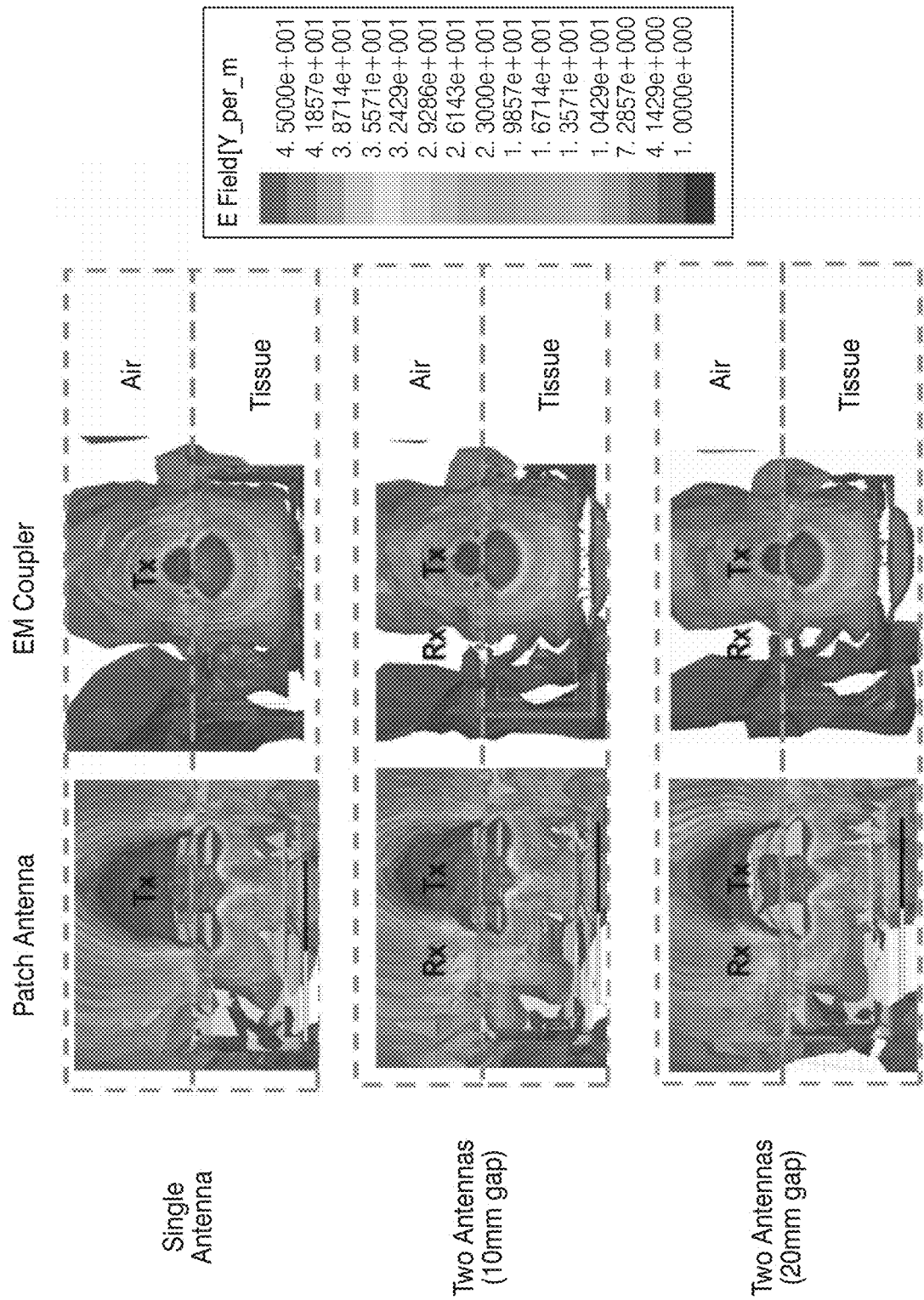
FIGS. 6C and 6D illustrate the improved energy coupling characteristics of the microwave sensors described herein as contrasted with primarily radiating structures, such as antennas.
Figure 6D:
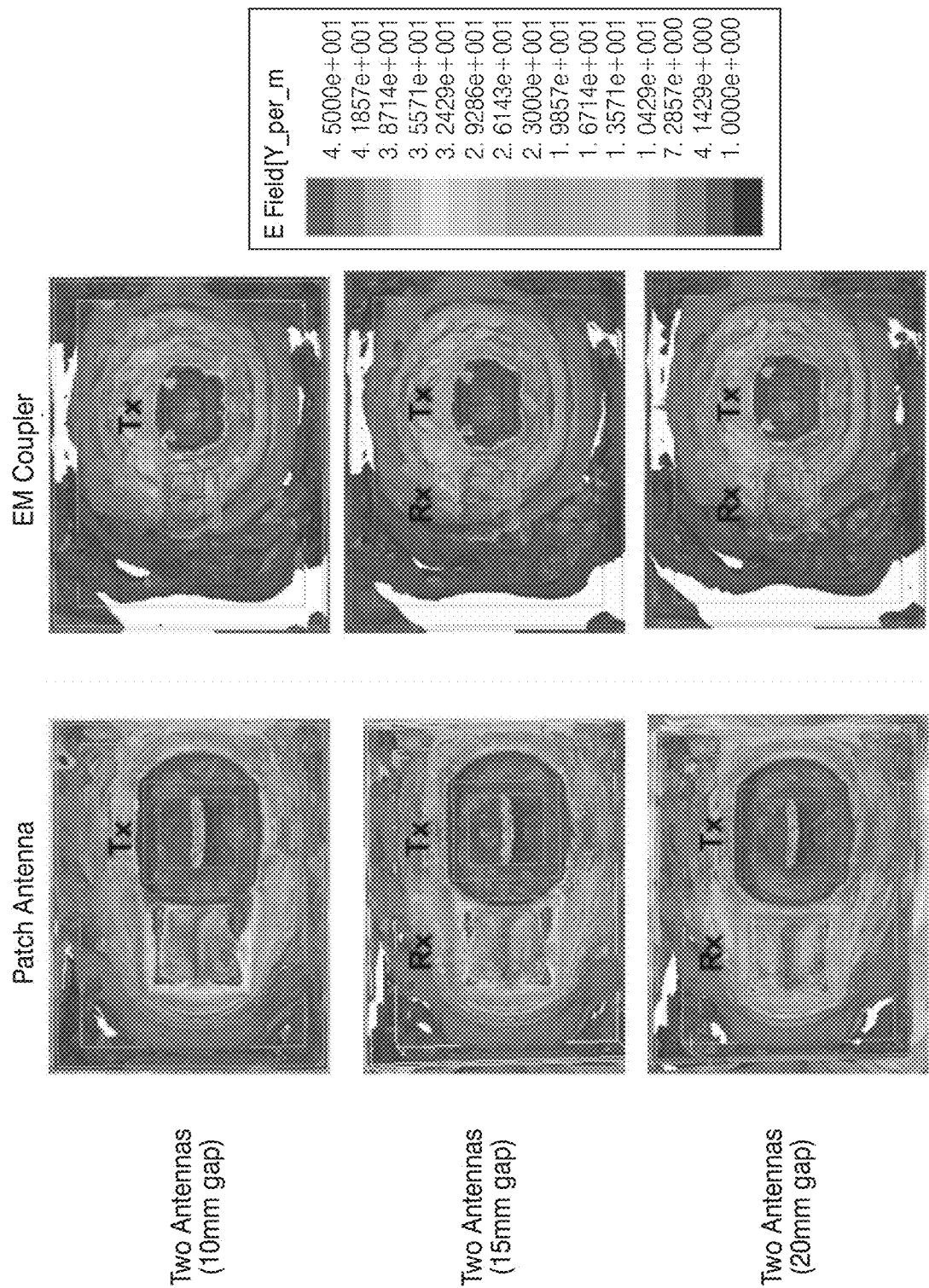

FIGS. 6C and 6D illustrate the improved energy coupling characteristics of the microwave sensors described herein as contrasted with primarily radiating structures, such as antennas. FIG. 6C includes cross-sectional views of simulated electrical fields resulting from antennas (left) as compared to the microwave sensors (i.e., electromagnetic (EM) couplers) described herein (right). Three separate cases are shown: a single transmitting device (top), transmitting and receiving devices in a side-by-side configuration with a 10 mm gap (middle), and transmitting and receiving devices in a side-by-side configuration with a 20 mm gap (bottom). As illustrated, antennas result in a much more significant amount of external leakage into the air and stronger mutual coupling between neighboring devices, whereas the microwave sensors described herein are significantly more effective in coupling microwave energy into the tissue in a localized manner. FIG. 6D shows top views of the same simulations from FIG. 6C. Once again, it is evident from FIG. 6D that the microwave sensors described herein are significantly more effective at coupling microwave energy into the tissue in a localized manner within the general footprint of the sensors.

In addition, the microwave sensors described herein have an advantage over antennas in that they can be based on transmission lines rather than primarily radiating structures. This is beneficial because it allows greater flexibility in terms of controlling the penetration depth of energy into the patient's body, as the transmission line-based microwave sensors described herein can more readily be operated at different frequencies. In transmission line-type microwave sensors, the size of the sensor is not necessarily determined by the operating frequency. In contrast, the size of radiating structures such as antennas is much more dependent on the operating frequency. Operating the transmission line-type microwave sensors at different frequencies facilitates retrieval of information at different depths inside the patient's body, where at higher frequencies the received information will be dominated by surface information and at lower frequencies the received information will be dominated by depth characteristics.

The fact that the microwave sensors described herein can be based on transmission line technology rather than radiating antenna technology means that they can have dimensions that are substantially frequency-independent. Instead, the size of the transmission line-based microwave sensors described herein can be largely based on the size of the area of contact between the sensor and patient needed to facilitate adequate energy coupling into the patient's body of a quasi-transverse electromagnetic mode guided between two conductors in a transmission line design. Thus, microwave sensors that are roughly the size of EKG patches can be capable of operating at frequencies as low as 700 MHz or as high as several GHz. This offers broadband capability to monitor surface as well as depth information, such as lung water content.

Figure 7:
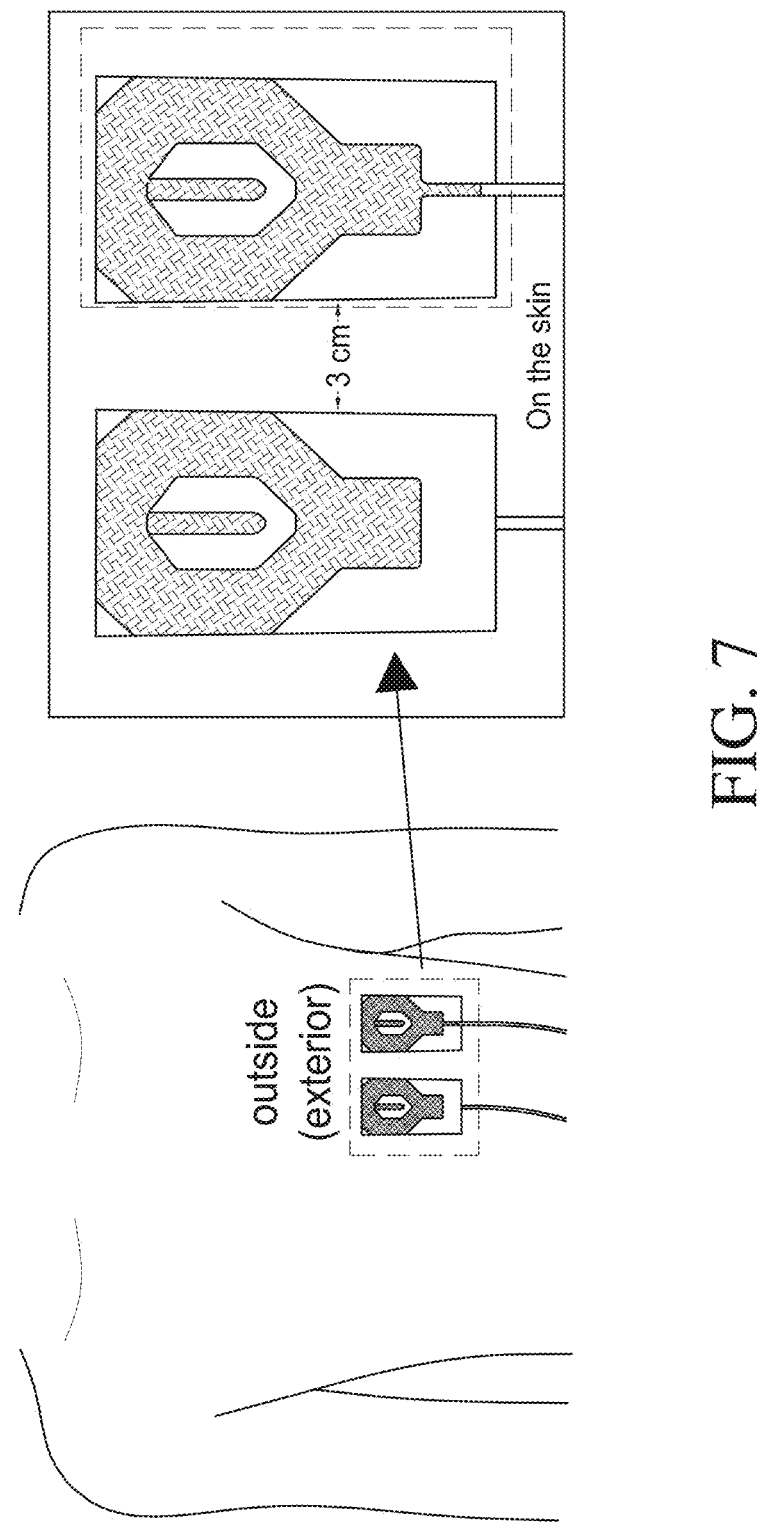
FIG. 7 shows the transmission and reception sensors mounted in side-by-side configuration in contact with the patient's chest.

FIG. 7 shows transmission and reception sensors mounted in side-by-side configuration in contact with the patient's chest. In an example of the side-by-side sensor unit, the microwave transmission sensor has a coplanar waveguide structure that is fabricated on a flexible substrate. In determining an optimum operating frequency for the microwave transmission sensor, tradeoffs may be made between desired depth of penetration in the human body (low frequency) and sensitivity to phase changes (high frequency). A preferred frequency range is from 700 MHz to 1.5 GHz, with an optimal range in the FCC allocated frequencies of 915 MHz and 920 MHz for medical and industrial applications (ISM band). For integrated vital signs detection that includes surface (EKG) and sub-surface (lung water and cardiac activity) measurements, it may be advantageous to use broadband sensors and multi-frequency measurements to better identify and possibly separate the various signals. With broadband sensors, the signal coefficients can be measured simultaneously at multiple frequencies, enabling monitoring of a patient's body at various penetration depths and eliciting maximum medical information.

As discussed in U.S. patent application Ser. No. 14/261, 884 (already incorporated by reference herein in its entirety), experimental results show that a separation distance of a few centimeters between side-by-side (SS) microwave sensors provides a good balance between SNR and sensitivity to vital signs. The side-by-side sensor configuration can be further optimized with adjustments in electromagnetic energy coupler design, including good impedance match between the microwave feed and sensor (e.g., while the sensor is in the as-worn position coupled to the patient's body), better energy distribution along the area of contact, insensitivity to human and other surrounding object's movements, and broadband characteristics.

As discussed herein, two or more microwave sensors can be provided in an array and each sensor can be used to transmit signals to, or receive signals from, any sensor in the array. These signals can be referred to as scattering parameter signals, which include transmission coefficient signals and reflection coefficient signals. A signal transmitted from one microwave sensor and received by another microwave sensor in the array can be referred to as a transmission coefficient signal. A signal transmitted and received at the same microwave sensor can be referred to as a reflection coefficient signal. In general, each signal can have a phase component and a magnitude component. These signals and/or there constituent components can be analyzed individually or collectively to determine a variety of physiological information about the patient. This is particularly true in the case of the described microwave sensors, as much of the received signals in the transmission coefficient measurements modes and the modification of the reflection coefficient values result from the interaction with and the scattering from the internal organs and tissue condition in the patient body, rather than direct and mutual coupling between measuring devices. Localizing electromagnetic energy coupling to the human body and reducing or minimizing mutual coupling between measuring devices can be important for achieving clear and uncorrupted data for the tissue conditions and status of internal organs.

Figure 8:
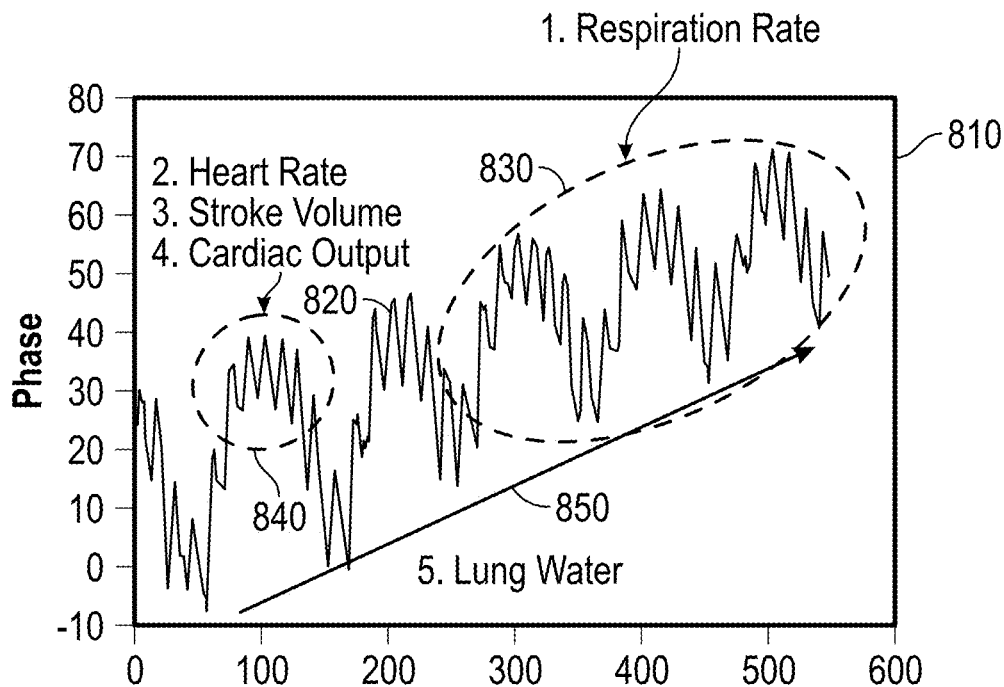
FIG. 8 includes a graph which illustrates that a transmission coefficient signal (e.g., the phase component of the signal) can be analyzed to determine respiration rate, heart rate, stroke volume, cardiac output, and lung water content.

FIG. 8 includes a graph 810 which illustrates that a transmission coefficient signal (e.g., the phase component of the signal) can be analyzed to determine, for example, respiration rate, heart rate, stroke volume, cardiac output, and lung water content. The graph 810 includes a curve 820 which plots the phase of the transmission coefficient between two microwave sensors in the side-by-side configuration illustrated in FIG. 7 as a function of time. Changes in the shape and characteristics of the waveform can be analyzed to calculate various physiological parameters. The curve 820 generally consists of a series of smaller-scale peaks superimposed on a series of larger-scale peaks. In this example, the physiological phenomenon which results in the larger-scale peaks has a greater effect on the measured phase of the transmission coefficient and the effect occurs over a relatively longer period of time. In contrast, the physiological phenomenon which results in the smaller-scale peaks has a smaller effect on the measured phase of the transmission coefficient and the effect occurs over a relatively shorter period of time.

The region 830 in the graph 810 includes three of the larger-scale peaks. These peaks result from the respiration of the subject and their frequency is indicative of the respiration rate. Meanwhile, the region 840 includes six of the smaller-scale peaks superimposed on a single larger-scale peak. These smaller-scale peaks are representative of the heart rate of the subject, which generally occurs on shorter time-scale, and causes smaller fluctuations in the phase of the transmission coefficient, than the respiration rate.

The graph 810 also includes a trend line 850. The trend of the curve 820 is sensitive to the pulmonary artery pressure and/or the lung water content of the subject. As discussed further with respect to FIG. 9, the curve 820 in FIG. 8 can be analyzed (e.g., by a digital signal processor) in order to determine the respiration rate, heart rate, stroke volume, cardiac output, and lung water content of the subject. The various peaks, trends, and other signal features can be isolated from one another using known signal processing techniques. A processed signal consisting predominantly of information from the smaller-scale peaks in the region 840 can be referred to as a heart signal or waveform; a processed signal consisting predominantly of information from the larger-scale peaks in region 830 can be referred to as a respiration rate signal or waveform; a processed signal consisting predominantly of trend information can be referred to as a lung water signal or waveform; etc.

Figure 9:
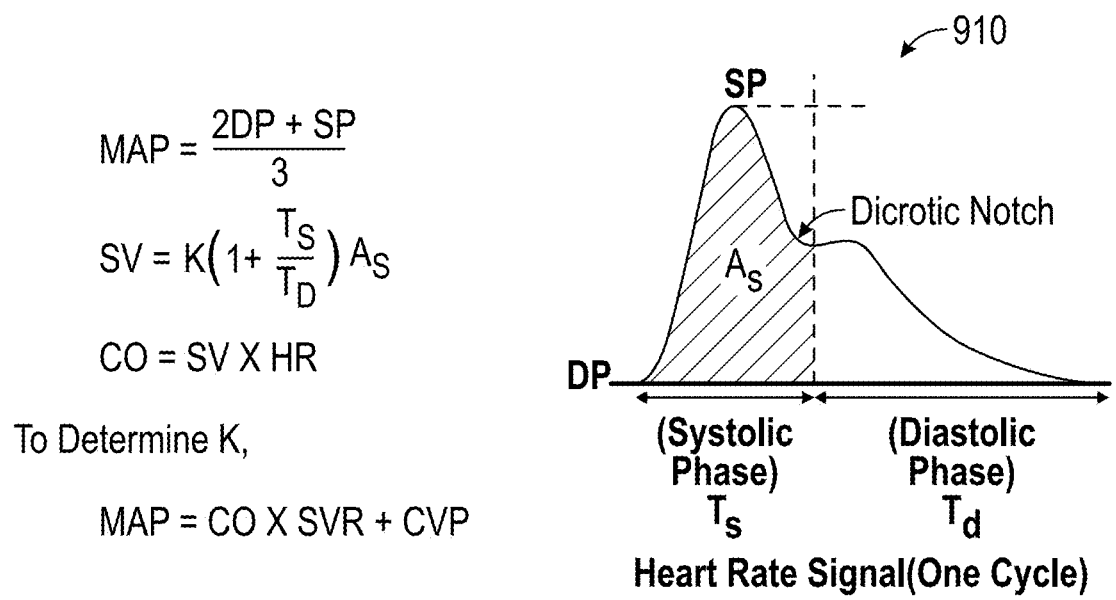
FIG. 9 illustrates how several physiological parameters can be calculated from a transmission coefficient signal (e.g., the phase component of the signal), such as the one illustrated in FIG. 8.

FIG. 9 illustrates how several physiological parameters can be calculated from a transmission coefficient signal (e.g., the phase component of the signal), such as the one illustrated in FIG. 8. The plot 910 is a magnified version of one cycle of the transmission coefficient signal. This can be extracted from the small signal variation 840 in FIG. 8. The shaded portion of the graph corresponds to the systolic phase ($T_s$), while the unshaded portion corresponds to the diastolic phase ($T_d$). The graph shows both the systolic peak (SP) and the diastolic peak (DP). As illustrated in FIG. 9, the mean arterial pressure can be calculated from the diastolic peak and the systolic peak. Alternatively, the mean arterial pressure is also related to the cardiac output (CO), the systemic vascular resistance (SVR), and the central venous pressure (CVP). The stroke volume (SV) can be calculated from the length of the systolic phase and the diastolic phase. The stroke volume also depends upon $A_s$, which is the area under the curve during the systolic phase. (If the parameter K in the equation for stroke volume is unknown, then stroke volume can instead be calculated from cardiac output.) The cardiac output can be calculated from the stroke volume and the heart rate.

As discussed herein, one physiological characteristic which is of clinical interest is lung water content. This information can be used in, for example, the diagnosis and treatment of congestive heart failure or other medical conditions. Heart-related (cardiogenic) pulmonary edema typically occurs when the left ventricle of the heart is not able to pump out blood at the same rate that it is received from the lungs. As a result, pressure increases inside the left atrium and in the pulmonary vasculature. This elevated pressure causes fluid to be pushed through the capillary walls into the air sacs of the lungs. Pulmonary edema, or excess fluid in the lungs, can be a very serious medical condition. Thus, the ability to monitor lung water content can prove to be a life-saving technology. Signals such as the transmission coefficient signals discussed herein can be used to monitor lung water content. Knowledge of lung water content is also important for patients with kidney disease and with Acute Respiratory Distress Syndrome (ARDS). Similar to the heart failure related medical complications, these diseases are associated with accumulation of water in patients' lungs that benefits from careful monitoring and management to prevent a hypotension condition, trauma, or even death.

Figure 10:
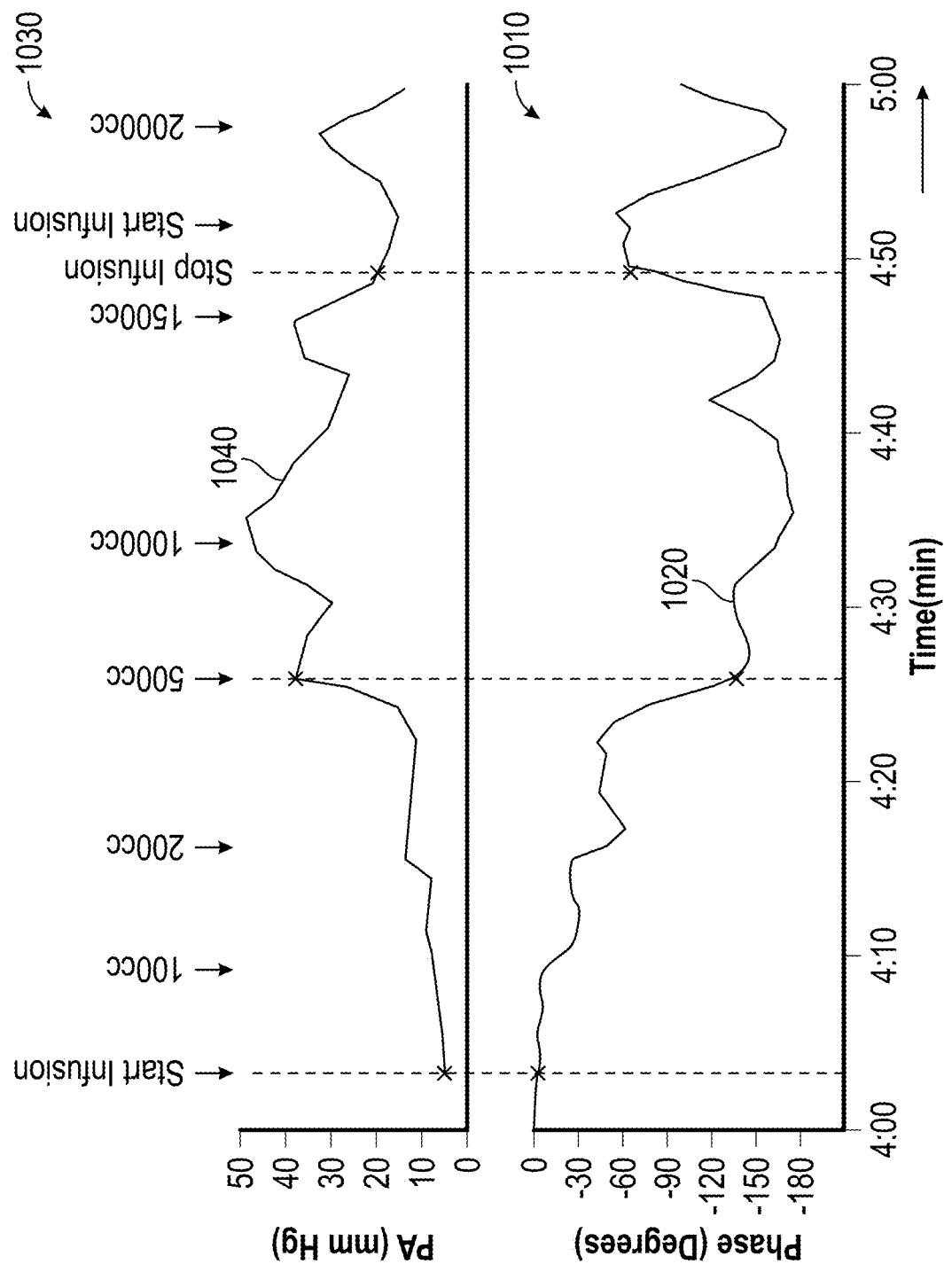
FIG. 10 includes a pair of graphs which show the sensitivity of the phase of the transmission coefficient (lower graph) when compared to the pulmonary artery pressure (upper graph) in a subject.

FIG. 10 includes a pair of graphs which show the sensitivity of the phase of the transmission coefficient (lower graph 1010) when compared to the pulmonary artery pressure (upper graph 1030) in a subject. (The plot in FIG. 10 does not include the respiration and heart rate peaks shown in FIG. 8 because it has been processed to show changes in lung water content vs. time (e.g., the trend line 850 in FIG. 8), not the raw transmission coefficient signal vs. time.) The lower graph 1010 includes a curve 1020 which plots the phase of the transmission coefficient between two microwave sensors in the side-by-side configuration illustrated in FIG. 7 as a function of time. The upper graph 730 includes a curve 1040 which plots the pulmonary artery pressure of the subject as a function of time while fluid is infused into the subject. The arrows at the top of the graphs show when the infusion of fluid begins, how much fluid is infused, and when the infusion ends. As illustrated by the top graph 1030, the infusion of fluid into the subject causes changes in the pulmonary artery pressure of the subject, resulting in changes in the phase of the microwave transmission coefficient (shown in the lower graph 1010).

Comparison of the lower graph 1010 to the upper graph 1030 reveals that the phase of the transmission coefficient is sensitive to changes in pulmonary artery pressure. Specifically, the phase of a sinusoidal signal transmitted by one of the microwave sensors to the other through the thorax of the subject is retarded between 0-180°, depending on the pulmonary artery pressure. The phase of the transmission coefficient becomes more negative when the pulmonary artery pressure increases. In addition, the slope of the phase graph goes toward zero when the slope of the pulmonary artery pressure graph also goes toward zero (with the phase tending to bottom out where the pulmonary artery pressure peaks). Thus, there is a strong correlation and relationship (in this case, an inverse relationship, though that is not always the case, as discussed herein) between the phase of the transmission coefficient and the pulmonary artery pressure in this particular example. The sensitivity of the phase of the transmission coefficient to changes in pulmonary artery pressure is very good, as changes in the latter directly result in changes to the former.

By measuring the phase of the transmission coefficient, it is thus possible to detect changes in the pulmonary artery pressure, which is related to the lung water content. Since the transmission coefficient between two microwave sensors correlates relatively well (albeit inversely in the illustrated example) to changes in the pulmonary arterial pressure and/or lung water content, the phase information provides the most sensitive indication to changes in lung water content, and hence the condition of the lung.

Although FIG. 10 illustrates a phase measurement for only a single frequency, in some embodiments, signals with multiple frequency components can be transmitted and the phase of the transmission coefficient for each frequency component can be measured in order to monitor pulmonary artery pressure and/or lung water content. For example higher frequencies may be used to emphasize surface and relatively shallow sub-surface conditions, while lower frequencies will provide deeper penetration in the body and hence reflect and provide more accurate information about this region.

While changes in the phase of the transmission coefficient between two microwave sensors are correlated to changes in pulmonary artery pressure and/or lung water content, the manner in which the phase responds to changes in pulmonary artery pressure and/or lung water content does not always behave in the same way that is illustrated in FIG. 10. For example, in some instances, the phase of the transmission coefficient may be directly correlated with pulmonary artery pressure, such that the phase advances in response to increases in pulmonary artery pressure and/or lung water content rather than retarding as in the illustrated example. The precise nature of the change in the phase of the transmission coefficient depends on a number of factors, including the placement of the microwave sensors on the thorax of the subject.

However, the phase of the transmission coefficient is not the only information available from the measured microwave signal(s). Indeed, the magnitude(s) of one or more frequency components in the transmitted microwave signal can also be measured. As discussed further herein, the magnitude of a transmission coefficient can be used to indicate whether a change in the phase of the transmission coefficient is indicative of improving lung condition (e.g., decreased pulmonary artery pressure and/or lung water content) or worsening lung condition (e.g., increased pulmonary artery pressure and/or lung water content).

As discussed with respect to FIGS. 8 and 9, the phase of the transmission coefficient between two microwave sensors can be used to measure a number of other vital signs in addition to pulmonary artery pressure and/or lung water content. However, as is the case with respect to pulmonary artery pressure and/or lung water content, the placement of the microwave sensors can affect the overall accuracy and reliability of the measurements of such vital signs. The sensor placement location which is best-suited to measure one vital sign may not be the best-suited to measure another. For example, a pair of side-by-side microwave sensors located with a clear "view" of the lung and minimal interference from other organs (e.g., the heart) may be best-suited for measuring lung water content. However, the same pair of sensors may not be best-suited for measuring heart rate or respiration rate. In view of this variability based on microwave sensor placement on the thorax, it may be advantageous for the monitoring system to include an array which includes additional microwave sensors placed at various locations on the thorax. By measuring the scattering parameters between each pair of microwave sensors in the array, it may be possible to improve the accuracy and reliability of various vital sign measurements. For example, different vital signs can be measured based on the scattering parameters between different pairs of microwave sensors.

Furthermore, as discussed herein, the magnitude of a transmission coefficient can be used to indicate whether a change in phase is indicative of improving or worsening lung condition. In a system which includes an array with multiple pairs of microwave sensors, the phase information can be obtained from the transmission coefficient between a first pair of microwave sensors (e.g., a pair located proximate the lower portion of the lung where fluid is apt to pool), while the magnitude information can be obtained from the transmission coefficient between a second pair of microwave sensors (e.g., a pair located so as to have an even clearer "view" of the lung). It should be understood, however, that the magnitude information from the same microwave sensor pair can also be used in some embodiments to confirm whether the measured phase information is indicative of improving or worsening lung condition.

Figure 11:
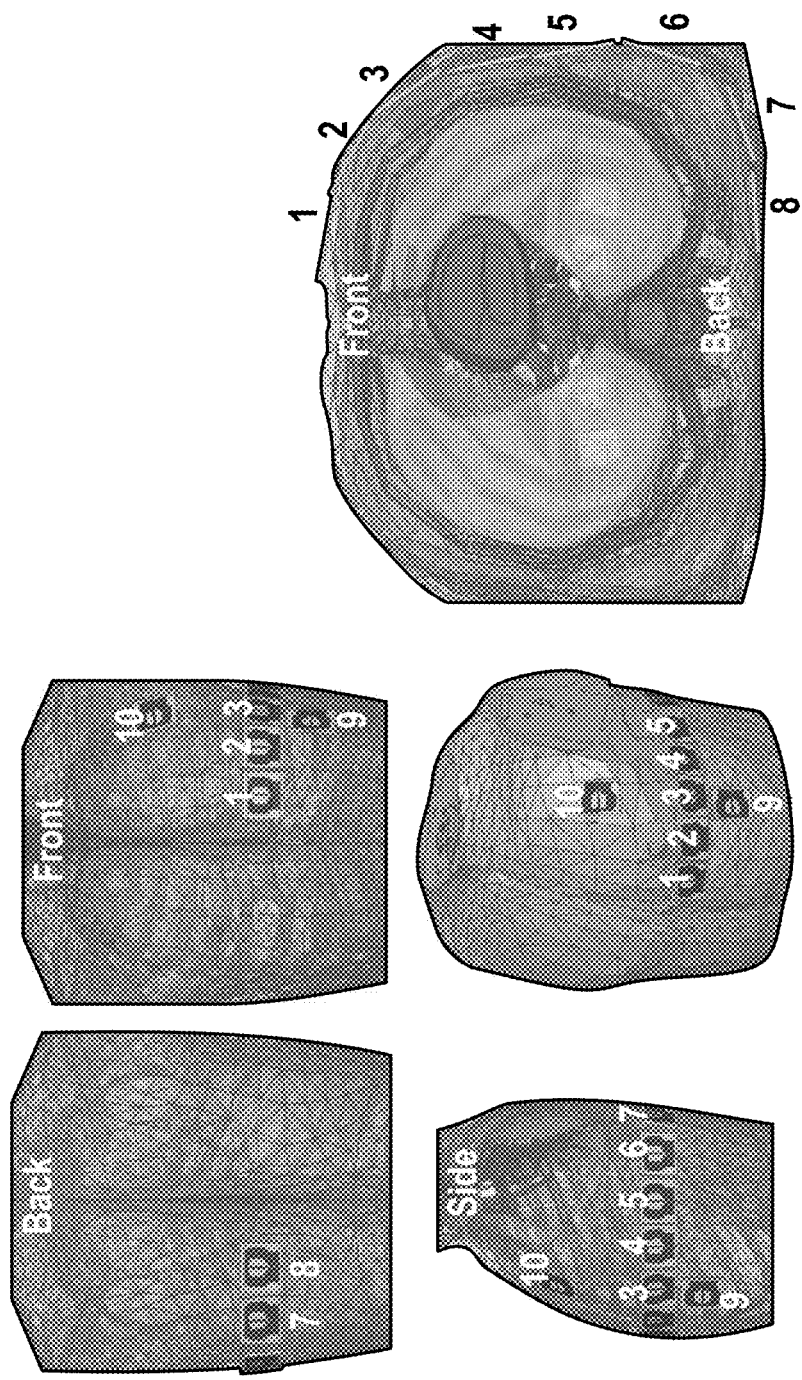
FIG. 11 illustrates an example of the placements of microwave sensors on the thorax of a human for a monitoring system that includes an array of microwave sensors.

FIG. 11 illustrates an example of the placements of microwave sensors on the thorax of a human for a monitoring system that includes an array of microwave sensors. (The illustrated array of sensors can be used in the calibration process described below.) Ten microwave sensors are illustrated and are numbered consecutively 1-10. Each microwave sensor has a unique placement on the thorax. The placements of the ten microwave sensors are shown by anterior, posterior, left lateral, top, and 45° anterior-lateral views of the thorax. As illustrated, in some embodiments, a horizontal row of microwave sensors (1-8) can be provided. Of these, three of the microwave sensors (1-3) are anteriorly located, three (4-6) are laterally located, and two (7-8) are posteriorly located. In addition to the horizontal row of microwave sensors, a sensor (9) is shown located nearer the lower extent of the lung and another sensor (10) is shown located nearer the heart. Although FIG. 11 illustrates 10 microwave sensors, a greater or lesser number of sensors can be used in different embodiments. Further, the specific placements of the microwave sensors illustrated in FIG. 11 are examples only; different and/or additional placements can also be used depending upon the application.

Of the placements illustrated in FIG. 11, microwave sensors 5-8 are those which would generally be expected to have the most unobstructed "views" of the lung. They provide lateral and posterior "views" of the lung which are relatively unobstructed by other organs or tissues. As discussed herein, in some embodiments, these sensors can advantageously provide magnitude information which accurately indicates whether measured changes in phase information are indicative of improving or worsening lung condition.

Figure 12:
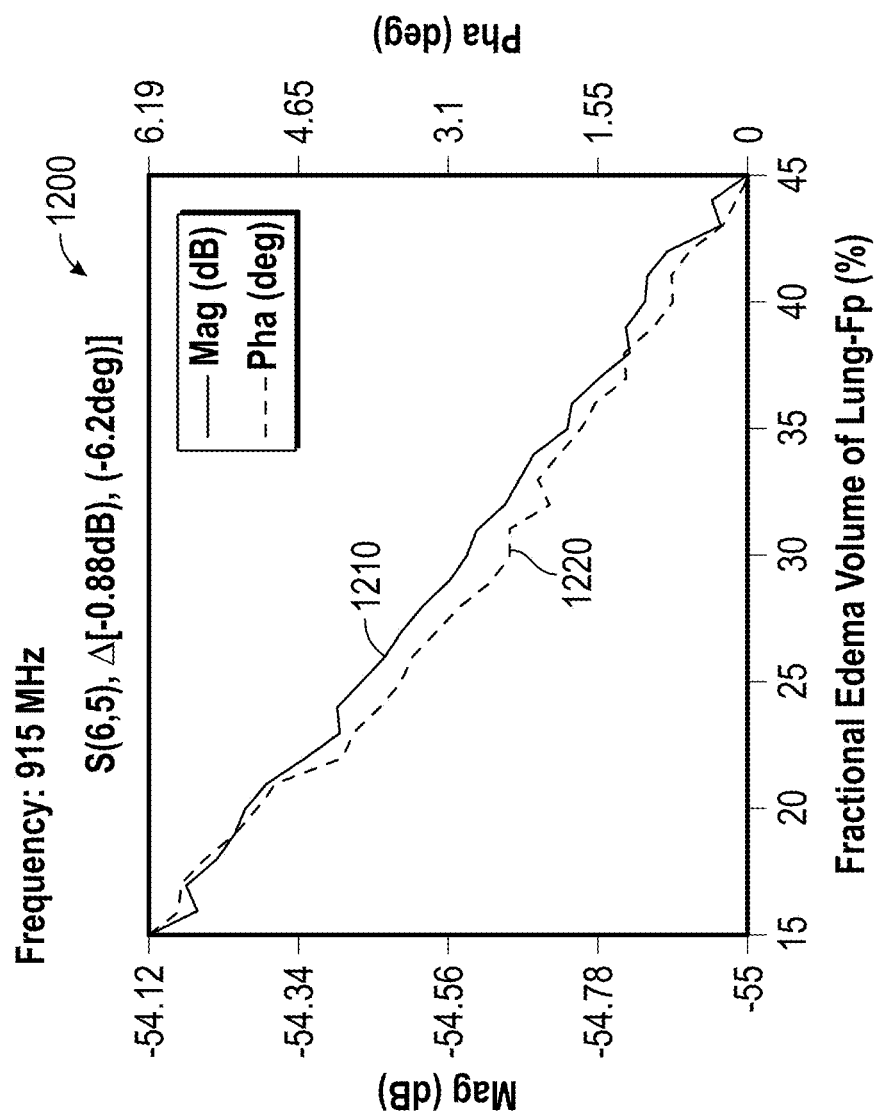
FIG. 12 includes a graph of the magnitude and phase of the transmission coefficient between the fifth and sixth microwave sensors illustrated in FIG. 11. These phase and magnitude changes are shown as a function of developing edema (increasing water content) in a lung. An increase in lung water content corresponds to an increase in the signal attenuation (increase in −dB) as the signal travels through the lung.
Figure 12:
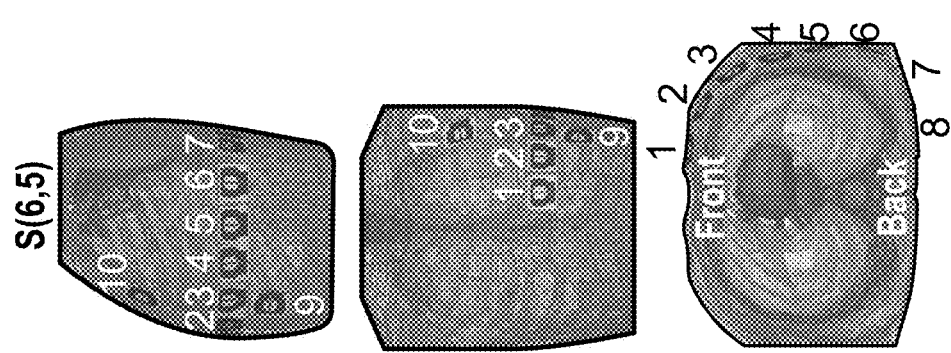

FIG. 12 includes a graph 1200 of the magnitude (solid curve 1210) and phase (dotted curve 1220) of the transmission coefficient between the fifth and sixth microwave sensors illustrated in FIG. 11. These signals have been processed to identify the trend line (e.g., similar to signal 850 in FIG. 8). The graph 1200 shows the response of the magnitude and phase of the S(6,5) transmission coefficient (i.e., the output signal measured at sensor 6 when sensor 5 is excited with an input signal) to changing fractional edema volume of a lung. As illustrated in FIG. 11, the fifth and sixth microwave sensors are adjacent sensors and are laterally located on the thorax. As such, it is expected that these sensors will have a relatively unobstructed "view" of the lung without substantial interference from other organs.

The graph 1200 shows that both the magnitude and phase of the S(6,5) transmission coefficient substantially monotonically decreased with increasing fractional edema volume of the lung. The magnitude scale has a range of 0.88 dB, while the phase scale has a range of 6.2°. Thus it may be noted that the phase changes are larger in values (number of degrees) than the changes in the magnitude (in dB). This is one indication that the phase is more sensitive to changes in lung water (while, as discussed further herein, the magnitude is more indicative of whether that change represents an increase or decrease in the amount of lung water).

Figure 13:
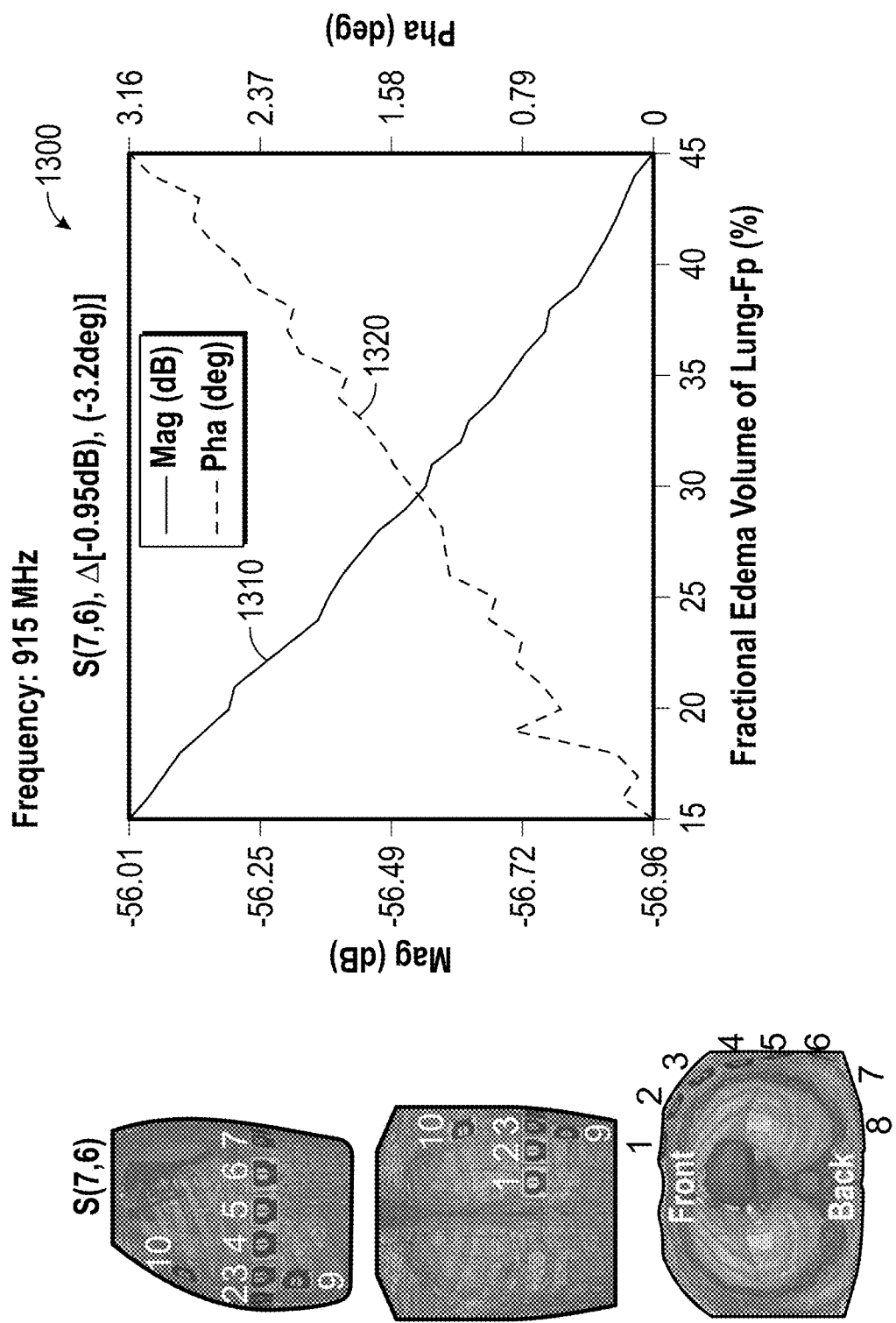
FIG. 13 includes a graph of the magnitude and phase of the transmission coefficient between the seventh and sixth microwave sensors illustrated in FIG. 11. Once again, the graph shows changes in the magnitude and phase of the transmission coefficient with an increase in the water content in a lung. The magnitude shows the increase in attenuation with increasing edema, while the relative phase of the transmission coefficient shows a trend opposite to the one measured between the fifth and sixth microwave sensors, as shown in FIG. 12.

FIG. 13 includes a graph 1300 of the magnitude (solid curve 1310) and phase (dotted curve 1320) of the transmission coefficient between the sixth and seventh microwave sensors illustrated in FIG. 11. The graph 1300 shows the response of the magnitude and phase of the S(7,6) transmission coefficient (i.e., the output signal measured at sensor 7 when sensor 6 is excited with an input signal) to changing fractional edema volume of the lung. Once again, as illustrated in FIG. 11, the sixth and seventh microwave sensors are adjacent. The sixth sensor is located laterally, while the seventh is located posteriorly. Again, it is expected that these sensors will have a relatively unobstructed "view" of the lung.

The graph 1300 is similar to the graph 1200 from FIG. 12 in that it shows that the magnitude of the transmission coefficient substantially monotonically decreased with increasing fractional edema volume of the lung. However, the graph 1300 is different from the graph 1200 in that it shows that the phase of the transmission coefficient actually increased with increasing fractional edema volume, rather than decreasing as shown in FIG. 12. This illustrates the fact that the phase response can vary depending on placement of the microwave sensors. The magnitude scale in FIG. 13 has a range of 0.95 dB, while the phase scale has a range of 3.2°.

Figure 14:
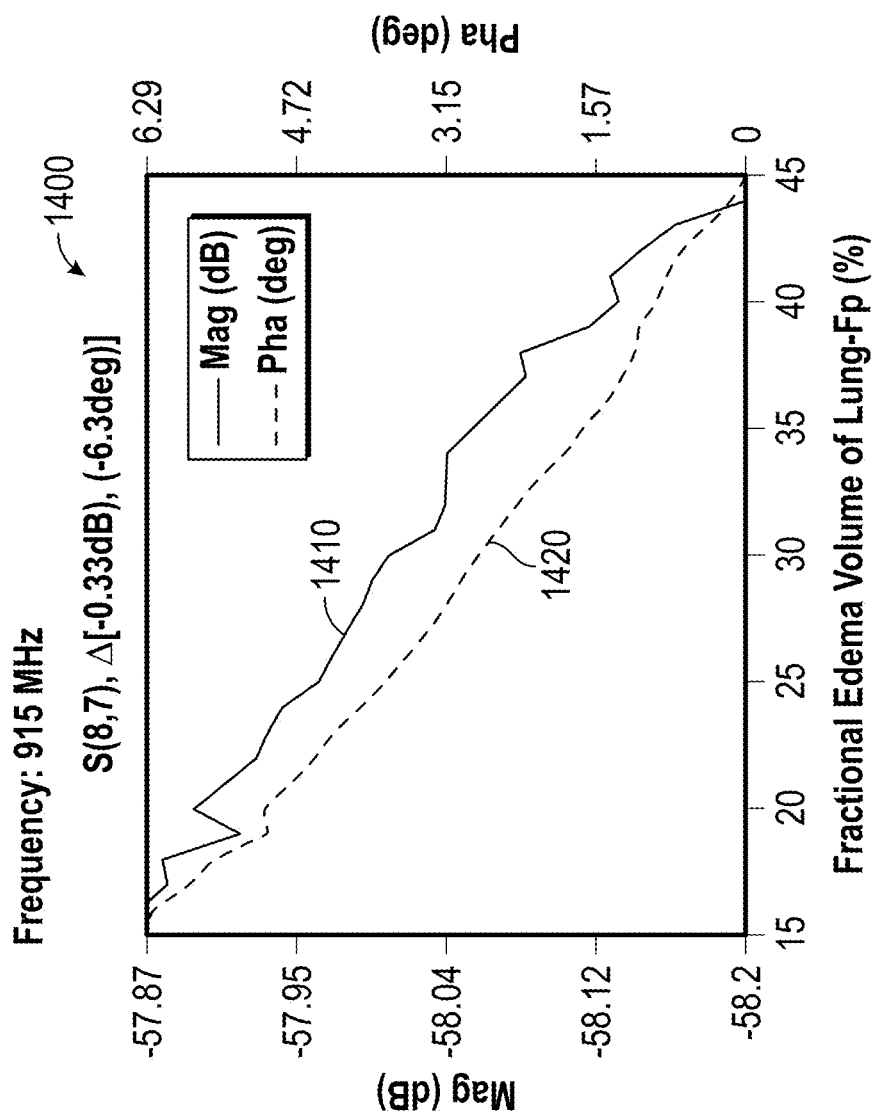
FIG. 14 includes a graph of the magnitude and phase of the transmission coefficient between the seventh and eighth microwave sensors illustrated in FIG. 11. The trends of the magnitude and phase measured between the seventh and eighth microwave sensors are similar to those measured between the fifth and sixth microwave sensors, as shown in FIG. 12.
Figure 14:
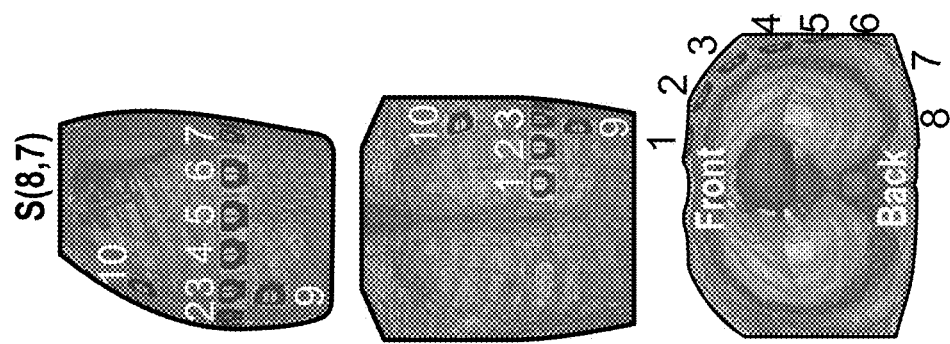

FIG. 14 includes a graph 1400 of the magnitude (solid curve 1410) and phase (dotted curve 1420) of the transmission coefficient between the seventh and eighth microwave sensors illustrated in FIG. 11. The graph 1400 shows the response of the magnitude and phase of the S(8,7) transmission coefficient (i.e., the output signal measured at sensor 8 when sensor 7 is excited with an input signal) to changing fractional edema volume of a lung. As illustrated in FIG. 11, the seventh and eighth microwave sensors are adjacent sensors and are posteriorly located on the thorax. Once again, it is expected that these sensors will have a relatively unobstructed "view" of the lung.

The graph 1400 is similar to both FIGS. 12 and 13 in that it shows that the magnitude of the S(8,7) transmission coefficient substantially monotonically decreased with increasing fractional edema volume of the lung. Further, like FIG. 12, but unlike FIG. 13, the phase of the S(8,7) transmission coefficient substantially monotonically decreased with increasing fractional edema volume. The magnitude scale in FIG. 14 has a range of 0.33 dB, while the phase scale has a range of 6.3°.

Figure 15:
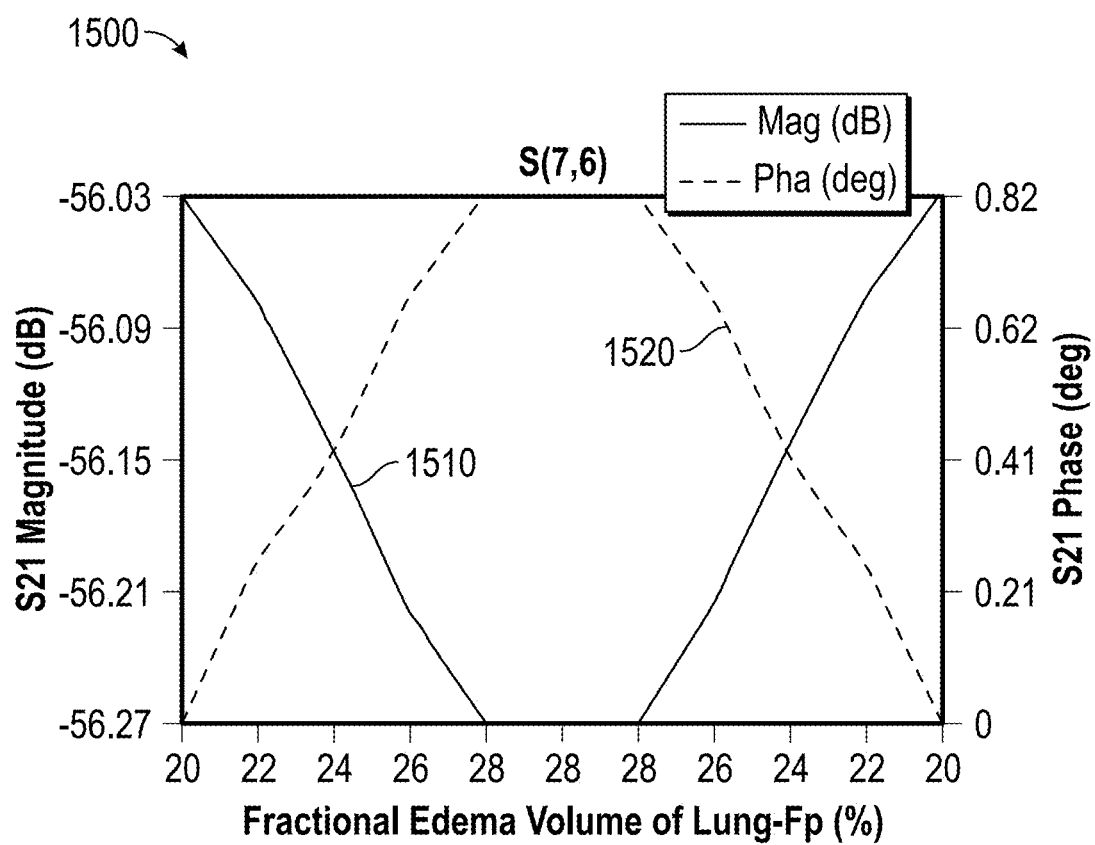
FIG. 15 includes a graph of the magnitude and phase of the transmission coefficient between the sixth and seventh microwave sensors illustrated in FIG. 11. These phase and magnitude changes are shown as a function first of increasing edema and then decreasing edema in a lung.

FIG. 15 includes a graph 1500 of the magnitude and phase of the transmission coefficient between the sixth and seventh microwave sensors illustrated in FIG. 11. These phase and magnitude changes are shown as a function first of increasing edema (from 20% to 28%) and then decreasing edema (from 28% to 20%) in a lung. As in FIGS. 12-14, the magnitude of the transmission coefficient in FIG. 15 decreases as edema increases. FIG. 15 illustrates, however, that the magnitude of the transmission coefficient also increases as edema decreases.

FIGS. 12-14 show results from the same increase in lung water content, but the measured phase (while indicating in every case that changes in lung water were occurring) showed changes in two different directions. FIGS. 12-14 show that the phases of transmission coefficients S(6,5) and S(8,7) both had a negative slope as lung water content increased. However, the phase of transmission coefficient S(7,6) increased with increasing lung water content. Notwithstanding the different behaviors of the phases in these figures, the commonality between all three figures is that the slopes of the magnitudes of the transmission coefficients S(6,5), S(7,6), and S(8,7) all decreased with increasing lung water content. This is likely due to the fact that increased lung water content causes more attenuation in the microwave signals, resulting in a decrease in the measured magnitudes of the transmitted microwave signals. Conversely, decreased lung water content would cause less attenuation in the microwave signals, resulting in a relative increase in the measured magnitudes of the transmitted microwave signals. Although this relationship between magnitude and lung water content may not necessarily be as well-defined for microwave sensors without a clear "view" of the lung due to electromagnetic scattering and interference effects from other organs and tissues, it does appear to hold true at least for sensors located in the clear viewing section for the lung. Thus, in some embodiments, the clear viewing of a section of the lung is important because of the correlation of the magnitude information from those sensors with changes in the amount of fluid accumulation in the lung. On the other hand, microwave sensors located in other positions may be better suited for providing information about other vital signs.

As discussed herein, in some embodiments, phase information—rather than magnitude information—from the microwave sensors can be most sensitively correlated with changes in lung water content and/or related metrics. However, as just discussed with respect to FIGS. 12-14, the phase information may be ambiguous in that, in some situations, neither positive nor negative changes in phase may be reliably indicative of improving or worsening lung condition. This can be so because phase is a relative parameter (i.e., an advance or delay with respect to a reference phase). Therefore, the phase may change in the positive or negative direction with a change in lung water content depending upon the reference phase. The reference phase, however, may depend on the size of the patient, sensor location, and even the sizes and locations of organs within the patient's body, resulting in possible ambiguity in the meaning of the phase measurements. The possible ambiguity of the phase information is not problematic when other independent information is available to help determine the condition of the lung. However, the possible ambiguity of the phase information can potentially be problematic in cases of stand-alone microwave monitoring, where no additional information is provided from a catheter or other comparative instrument.

However, since the magnitudes of transmission coefficients between microwave sensors located in the clear viewing section for the lung reliably decrease with increased lung water content, and conversely increase with decreased lung water content, such magnitude information can be used in conjunction with phase information to both sensitively detect changes in lung water content and determine whether those changes indicate improving or worsening lung condition. As a solution to the potential problem of phase information ambiguity, magnitude information can be used to clarify whether a change in lung water content indicated by a phase change is indicative of increasing or decreasing lung water content (or a related parameter).

In some embodiments, one or more microwave signals are transmitted into the thorax of a patient using one or more microwave sensors, as discussed herein. This can include, for example, a microwave signal transmitted through the thorax between side-by-side microwave sensors. The raw signal can then be pre-processed, as described herein, to obtain information indicative of lung water content (e.g., trend line data can be obtained from the raw signal). The phase information can then be analyzed to determine whether the lung water content (or a related parameter) has changed. For example, a digital signal processor can analyze the slope of the phase information of the lung water signal over time to determine whether the phase is increasing or decreasing. As discussed herein, such fluctuations may reliably be correlated with changes in lung water content. Meanwhile, the magnitude of one or more microwave signals can be analyzed (e.g., by a digital signal processor) to determine whether a change indicated by the phase information is indicative that lung water content (or a related parameter) is increasing or decreasing.

For example, the slope of the magnitude information of the lung water signal over time can be analyzed to determine whether the magnitude information is increasing or decreasing. If the magnitude information is decreasing over time (i.e., greater attenuation of the microwave signal), then the digital signal processor may determine that the change in phase information is indicative of increased lung water content and worsening lung condition. Alternatively, if the magnitude information is increasing over time (i.e., less attenuation of the microwave signal), then the digital signal processor may determine that the change in phase information is indicative of decreased lung water content and improving lung condition. The digital signal processor can then provide an appropriate output signal to a display, a light, a speaker, etc. to indicate that the lung water content (or a related parameter) is improving or worsening.

In some cases, the magnitude information may be obtained from microwave sensors in the clear viewing section for the lung (e.g., the sensors may be laterally or posteriorly located with respect to the lung). The magnitude information may be obtained from the same pair of microwave sensors used to provide the phase information. Alternatively, the magnitude information may be obtained from a different pair of sensors. In addition, the phase and magnitude information may be obtained and analyzed at a single frequency (e.g., 915 MHz or 2.4 GHz) or at multiple frequencies. The measured frequency or frequencies can be the same or different for the phase and magnitude information, respectively.

In some embodiments, specific microwave sensors can be selected a priori for making the vital sign measurements discussed herein. The same or different sensors can be used for different vital sign measurements, or for different aspects of a single vital sign measurement (e.g., for providing the phase and magnitude information in a lung water measurement). However, in other embodiments, specific microwave sensors are not selected a priori. Instead, an automated calibration method can be performed in order to select which microwave sensors are used to perform a given vital sign measurement. This can be advantageous in some embodiments due to, for example, variations in sensor placement and/or patient size. In some embodiments, the automated calibration method can include performing a scan of the microwave scattering parameters for the array of microwave sensors.

FIG. 16 is a chart of the magnitude and phase of the complete set of scattering parameters for a monitoring system which includes an array of microwave sensors. FIG. 16 illustrates the magnitude and phase values for the transmission coefficients between each pair of microwave sensors at one moment in time. It also illustrates the magnitude and phase values for the reflection coefficients of each individual microwave sensor at one moment in time. Although the chart in FIG. 15 includes measurements for all of the transmission and reflection coefficients for the array of microwave sensors, in some embodiments only the transmission coefficients for adjacent side-by-side pairs of microwave sensors are obtained.

The information shown in FIG. 16, or a subset thereof, can be obtained for a single frequency or for multiple different frequencies. In addition, it can be obtained at a single instant in time or at multiple instants over the course of a period of time to obtain a collection of scattering parameter signals. Once all or a portion of the scattering parameter information has been obtained, it can be analyzed (e.g., by a digital signal processor) to select which microwave sensor data will be used to perform a given vital sign measurement.

In some embodiments, microwave sensor data can be selected for use in a particular vital sign measurement based on how closely a parameter calculated from the data set in question correlates with a known or measured physiological characteristic at an initial time or on a continuing basis. For example, the signal from the pair of microwave sensors which yields a mean arterial blood pressure (MAP) measurement (e.g., calculated as discussed with respect to FIG. 9) which most closely correlates with an initial or continued reference MAP measurement can be selected. In some cases, the reference MAP measurement can be obtained from another instrument, such as a catheter inserted into the patient's body. Correlation to mean arterial blood pressure is just one example of a physiological criterion which can be used to guide the selection of sensor data for calculating a given vital sign. Other physiological criteria can also be used.

As just mentioned, microwave sensor data can be selected for use in a particular vital sign measurement based on the data's correlation to a measurement of a physiological characteristic, such as mean arterial pressure, from an external device. However, in some embodiments, microwave sensor data can also be selected based on its correlation to the data obtained from other pairs of sensors in the microwave array. For example, mean arterial pressure can be determined based on data collected from one pair of microwave sensors in the array. As discussed herein (e.g., with respect to FIG. 9), mean arterial pressure can be obtained from a measured heart waveform. In some embodiments, the measured heart waveform may be obtained from the microwave sensor pair located nearest the heart.

Once the heart waveform has been obtained, the mean arterial pressure can be calculated and designated as a standard to be compared with data from other microwave sensors in the array. For example, as discussed herein, data from sensors located with a "view" of the lung can be used to determine whether lung water content is changing and whether the condition of the lung is improving or worsening. If more than one pair of sensors has a "view" of the lung, in some embodiments, the data from each such pair of sensors can be correlated with the designated standard mean arterial pressure measurement (whether determined from an external instrument or from the microwave system itself). This can be done, for example, by determining one or more additional mean arterial pressure values from the waveforms obtained from the sensors with a "view" of the lung. These arterial pressure values can be compared with the designated standard arterial pressure value. The data from the pair of sensors which is designated as correlating best with the standard mean arterial pressure value (e.g., as determined using known statistical and signal processing techniques) can be selected by the processor as the data most indicative of the condition of the lung because lung water content is correlated with arterial pressure. The processor can analyze the selected data to monitor lung water content in the patient.

Figure 17:
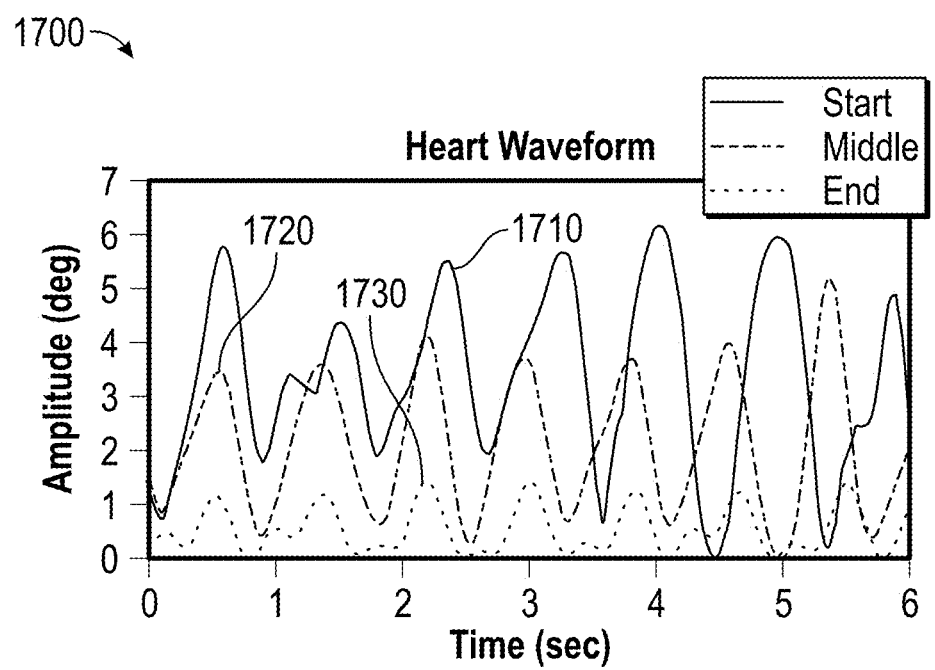
FIG. 17 includes a graph of a transmission coefficient signal (e.g., the phase component of the signal) corresponding to a heart waveform for a dialysis patient. The graph shows that the magnitude and shape of the heart waveform changes with changing blood pressure during the dialysis process.

FIG. 17 includes a graph of a transmission coefficient signal (e.g., the phase component of the signal) corresponding to a heart waveform for a dialysis patient. The graph includes a first curve 1710 which was measured at the start of the dialysis process, a second curve 1720 measured in the middle of dialysis, and a third curve 1730 measured at the end of dialysis. These curves show that the magnitude and shape of the heart waveform changes with changing blood pressure during the dialysis process. This data provides further evidence that a heart waveform obtained using the microwave system described herein can be used to determine a measure of arterial pressure. Thus, in some embodiments, a processor analyzes the heart waveform (including its magnitude, shape, and other characteristics) to determine the blood pressure of the patient. This can be done using, for example, the technique described and shown with respect to FIG. 9. As just discussed, this measurement can be used in a calibration process to select data from other sensors in the array from which to monitor edema of the lungs.

Figure 18A:
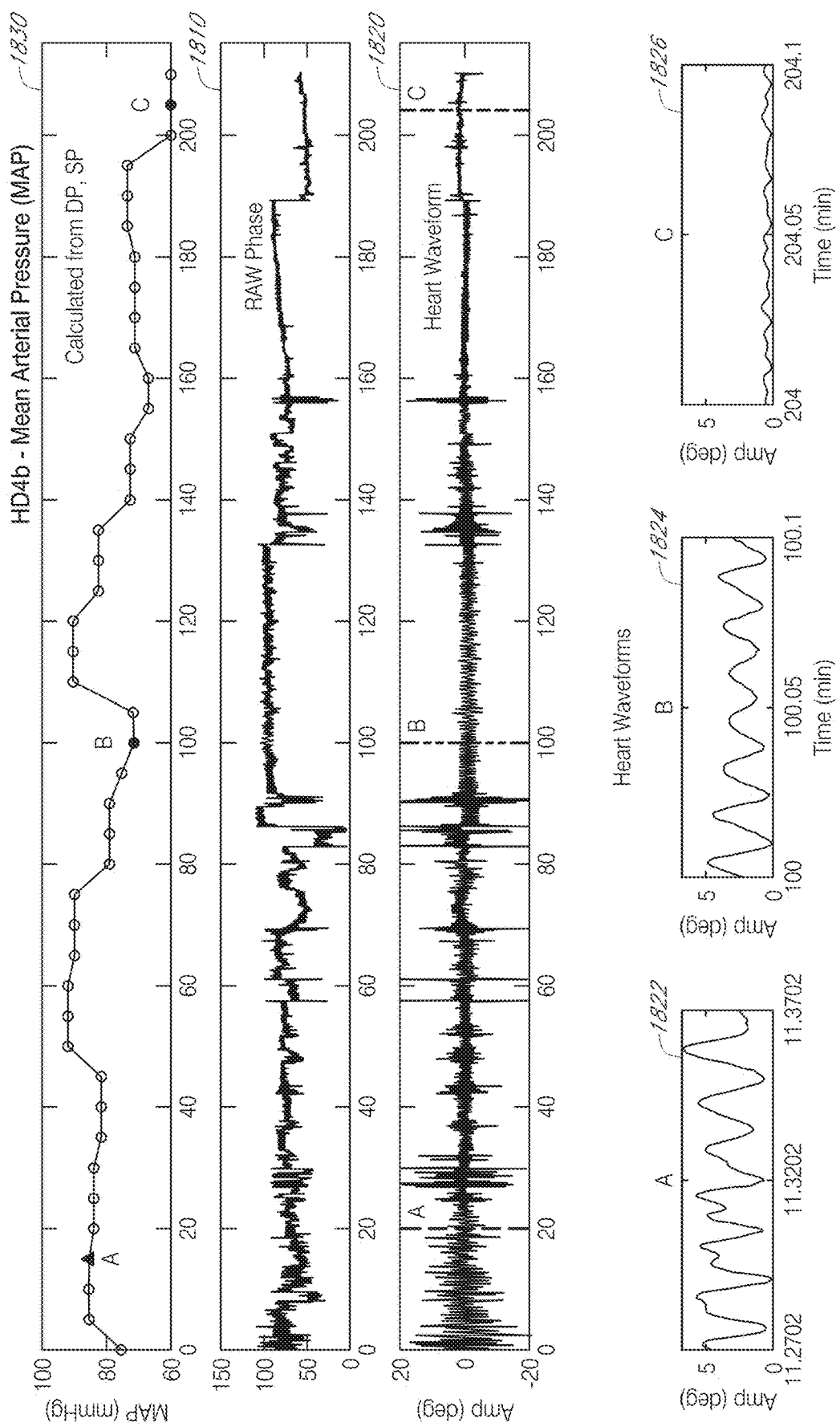
FIGS. 18A and 18B also show clinical data collected from a dialysis patient using the microwave system described herein.
Figure 18B:
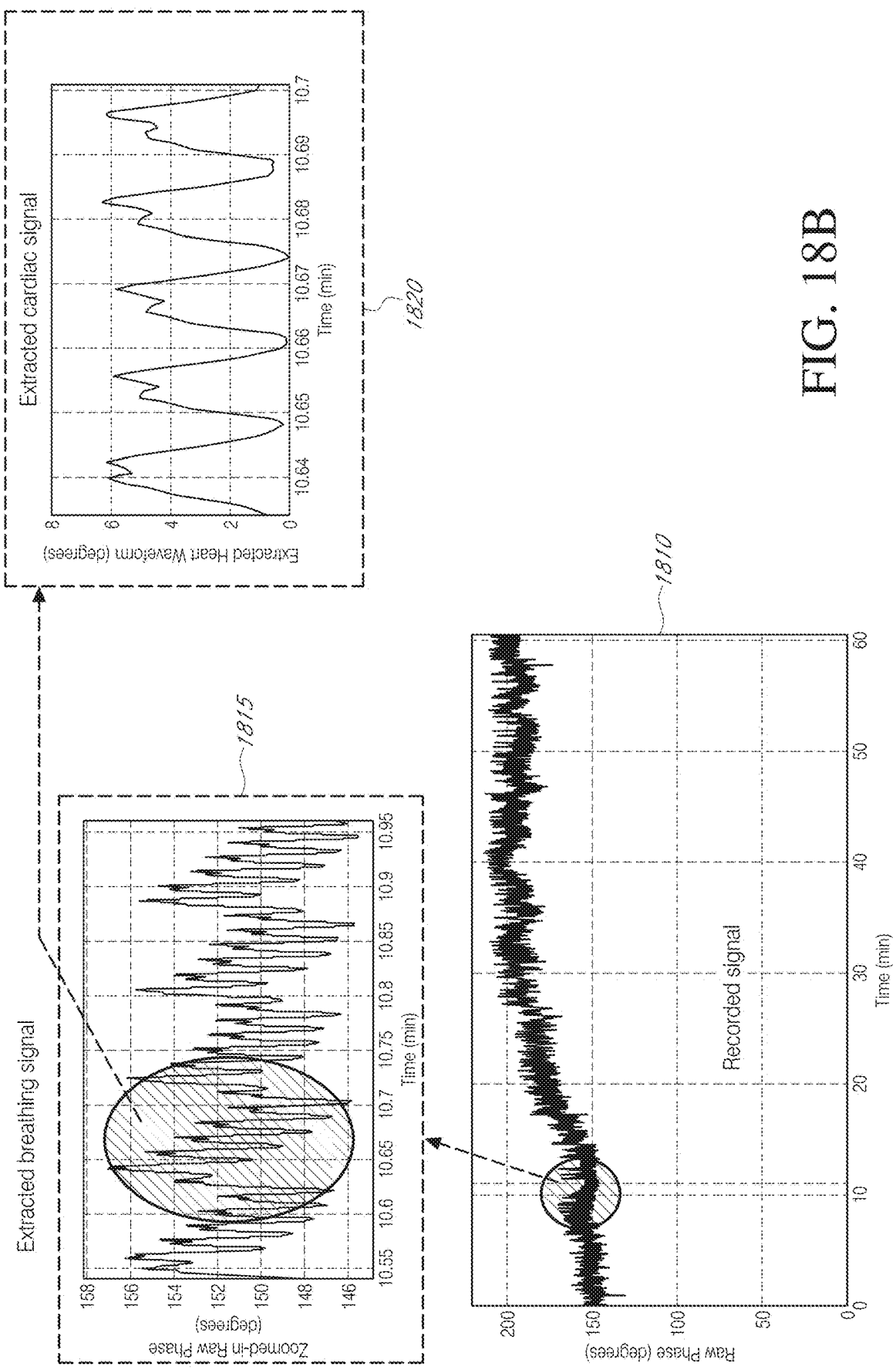

FIGS. 18A and 18B also show clinical data collected from a dialysis patient using the microwave system described herein. FIG. 18A includes a graph 1810 of the phase of a raw transmission coefficient signal collected using the microwave system. A similar raw phase signal is shown in graph 1810 of FIG. 18B. The raw transmission coefficient signal in graph 1810 was processed, using the techniques disclosed herein, to obtain the heart waveform shown in graph 1820. A similar heart waveform is shown in graph 1820 in FIG. 18B. (FIG. 18B also shows a possible intermediate step of calculating a signal shown in graph 1815, which includes a heart waveform superimposed on a breathing waveform.) After the heart waveform in graph 1820 was obtained, it was processed, using the techniques disclosed herein, to obtain a mean arterial pressure waveform which is shown in graph 1830. The mean arterial pressure waveform in graph 1830 shows that the dialysis patient's blood pressure decreased from time A to time B to time C as the volume of the patient's blood was reduced due to the dialysis process.

FIG. 18A also shows magnified views of the heart (cardiac) waveform at time A (shown in graph 1822), time B (shown in graph 1824), and time C (shown in graph 1826). These magnified views of the heart waveform show that its peak-to-trough amplitude was greatest at time A when the patient's mean arterial pressure was the highest, that the peak-to-trough amplitude was smaller at time B when the patient's mean arterial pressure had been reduced due to decreased blood volume, and that the peak-to-trough amplitude was smallest at time C when the patient's mean arterial pressure was likewise the smallest. These heart (cardiac) waveforms are representative of Starling's Law, which generally provides that the stroke volume of the heart increases with increasing blood volume and decreases with decreasing blood volume. In other words, the strength with which the left ventricle contracts increases with increasing end atrial diastolic volume and decreases with decreasing end atrial diastolic volume. This clinical data provides further confirmation that the heart (cardiac) waveforms measured by the microwave system described herein can provide extremely valuable clinical data.

Figure 19:
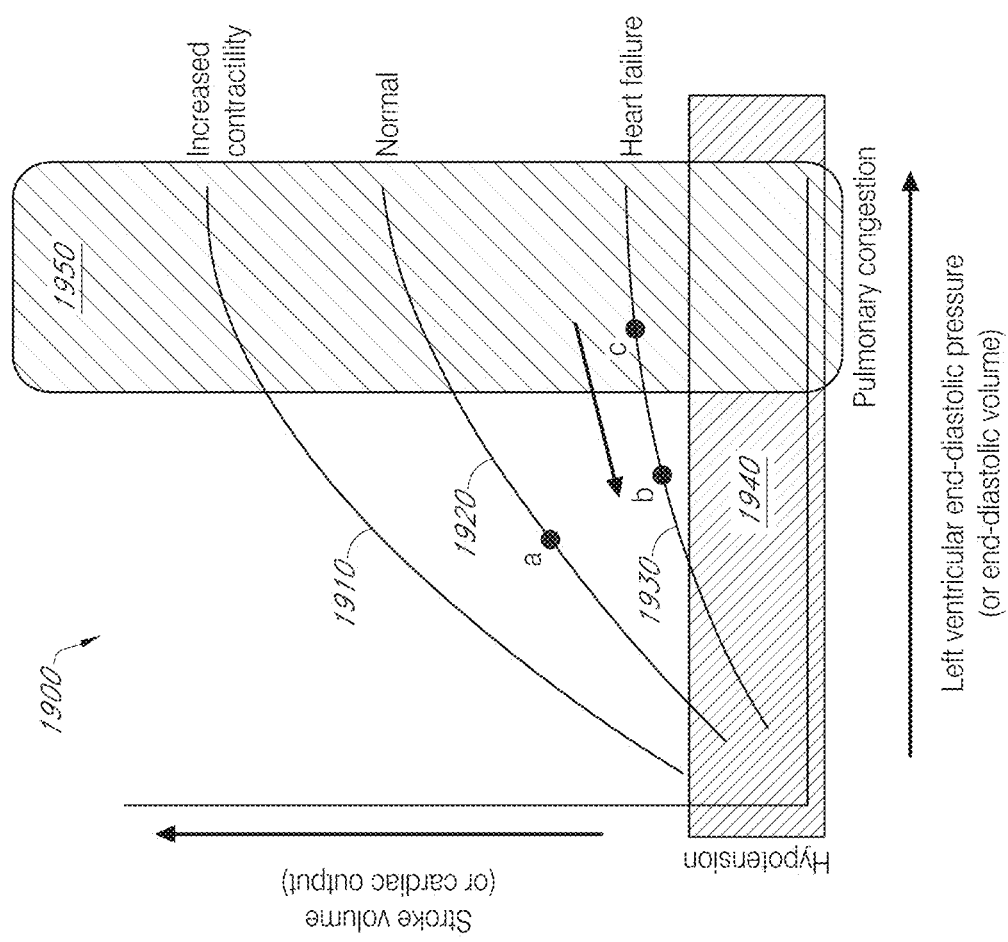
FIG. 19 shows a graphical representation of Starling's Law and illustrates how the microwave system described herein can be used to assist in treatment of patients with congestive heart failure or patients undergoing dialysis.

FIG. 19 shows a graphical representation of Starling's Law and illustrates how the microwave system described herein can be used to assist in treatment of patients with congestive heart failure or patients undergoing dialysis. The graph 1900 in FIG. 19 plots stroke volume as a function of left ventricular end diastolic pressure. As shown by curves 1910, 1920, in 1930, stroke volume increases with increasing end diastolic pressure in accordance with Starling's Law. When diastolic pressure is too low, the patient is exhibiting hypotension, as shown by the shaded region 1940. When diastolic pressure increases beyond the limits of the heart's ability to further increase stroke volume, the curves 1910, 1920, and 1930 begin to level off. When this occurs, pressure increases in the pulmonary vasculature, which causes fluid to pass through the capillary walls into the lungs resulting in pulmonary congestion. This is shown by the shaded region 1950.

Point a on the middle curve 1920 is representative of the normal operating condition of the heart in a normal patient. The top curve 1910 is that of a patient whose heart is exhibiting higher-than-normal contractility. Meanwhile, point c on the bottom curve 1930 is representative of the operating condition of a patient who is experiencing heart failure and associated pulmonary congestion. This condition represents a medical emergency which can be relieved by reducing end diastolic pressure, such as for example by reducing the patient's blood volume using diuretics or other techniques. The goal of such treatment is to cause the patient's heart to transition toward point b on the lower curve 1930, as illustrated by the arrow. However, as is evident from the graph, if the treatment is taken too far the patient will experience hypotension. It would therefore be advantageous to use the signals provided by the microwave system described herein to provide real-time monitoring and feedback regarding the efficacy of the treatment for congestive heart failure. This can be done by, for example, monitoring the peak-to-trough amplitude of the heart signals shown in FIG. 18A. Similarly, this technique can be used to prevent hypotension in dialysis patients. The microwave system described herein is particularly advantageous for these and other applications because it is capable of providing real-time, non-invasive, accurate data regarding the physiological condition of the heart, lungs, and vasculature.

In some embodiments, isolated lung experiments can be performed in order to understand, quantify, and/or calibrate the impact of various diseases on lung water content, the distribution of water in the lung, and the effect of such processes on the signals measured by the microwave system described herein. In such embodiments, a lung can be removed and isolated from a subject. Blood or other fluid can be infused directly into the isolated lung using a pump. The pump can also pump fluid out of the isolated lung as desired. The isolated lung can be positioned on a scale and the weight of the lung can be used as a control measurement of the lung water content at any point during the experiment. The isolated lung can also be connected to a mechanical respirator which pumps air into the isolated lung in order to simulate respiration during the experiment. Microwave sensors can be placed directly on the isolated lung to collect data, as described herein, throughout the experiment. This type of isolated lung experiment can be a valuable tool for developing an understanding of the effect of lung water content clinically and physiologically.

In some embodiments, when an array of microwave sensors is used in the microwave instrument disclosed herein, the array of received signals may be combined using a reconstruction algorithm to provide an image of the water distribution in the lung. Different sensors in the array can be excited at different frequencies to allow, for example, targeted measurement of specific vital signs. For example, an anterior sensor in the array can be excited at 2.4 GHz to measure heart rate. The same or a different anterior sensor can be excited at 915 MHz to measure breathing rate. A lateral or posterior sensor in the array can be excited at 915 MHz to perform a lung water measurement, etc. It should be understood, however, that these are only examples; different frequencies besides the ones mentioned can be used. Further, microwave sensors located in different positions than the ones just mentioned can be used to perform various vital sign measurements.

The embodiments described throughout the attached specification, drawings, and claims have been described at a level of detail to allow one of ordinary skill in the art to make and use the devices, systems, methods, etc. described herein. A wide variety of variation is possible. Components, elements, and/or steps may be altered, added, removed, or rearranged. For example, method steps can be practiced all together or in any sub-combination. Similarly, claim limitations can be separated and/or combined and included in any combination or sub-combination.

The devices, systems, and methods described herein can advantageously be implemented using, for example, computer software, hardware, firmware, or any combination of software, hardware, and firmware. Software modules can comprise computer executable code for performing the functions described herein. In some embodiments, computer-executable code is executed by one or more general purpose computers (including desktop computers, notebook computers, tablet computers, smart phones, etc). However, a skilled artisan will appreciate, in light of this disclosure, that any module that can be implemented using software to be executed on a general purpose computer can also be implemented using a different combination of hardware, software, or firmware. For example, such a module can be implemented completely in hardware using a combination of integrated circuits. Alternatively or additionally, such a module can be implemented completely or partially using specialized computers designed to perform the particular functions described herein rather than by general purpose computers. In addition, where methods are described that are, or could be, at least in part carried out by computer software, it should be understood that such methods can be provided on non-transitory computer-readable media (e.g., optical disks such as CDs or DVDs, hard disk drives, flash memories, diskettes, or the like) that, when read by a computer or other processing device, cause it to carry out the method.

A skilled artisan will also appreciate, in light of this disclosure, that multiple distributed computing devices can be substituted for any one computing device illustrated herein. In such distributed embodiments, the functions of the one computing device are distributed such that some functions are performed on each of the distributed computing devices.

The devices described herein can exchange information with each other, or with other devices, via one or more communication channels. Such communication channels can be wired or wireless, and can include networks, such as a Local Area Network, a Wide Area Network, the Internet, etc.

While certain embodiments have been explicitly described, other embodiments will become apparent to those of ordinary skill in the art based on this disclosure. Therefore, the scope of the invention is intended to be defined by reference to the claims and not simply with regard to the explicitly described embodiments.

What is claimed is:

1. A method of monitoring lung water content of a patient using a plurality of microwave sensors, the method comprising:
    transmitting a plurality of microwave signals into the thorax of a patient using the microwave sensors;
    receiving a plurality of the microwave signals using the microwave sensors, the plurality of received microwave signals each comprising at least one frequency component having a magnitude and a phase;
    analyzing the phase of the received microwave signal corresponding to a first pair of the microwave sensors to monitor changes in the lung water content; and
    analyzing the magnitude of the received microwave signal corresponding to a second, different pair of the microwave sensors to determine whether the change in lung water content indicated by the received microwave signal corresponding to the first pair of microwave sensors is increasing or decreasing.

2. The method of claim 1, further comprising:
    determining that the lung water content is increasing if the magnitude is decreasing; and
    determining that the lung water content is decreasing if the magnitude is increasing.

3. The method of claim 1, wherein the second pair of microwave sensors is located laterally or posteriorly on the patient's thorax in a viewing area for the lung that is unobstructed by another internal organ.

4. The method of claim 1, further comprising:
    analyzing the received microwave signal corresponding to a pair of the microwave sensors located adjacent to the heart of the patient to determine a blood pressure indicator.

5. The method of claim 4, further comprising selecting the received microwave signal corresponding to the second pair of microwave sensors based on correlation with the blood pressure indicator.

6. The method of claim 1, wherein the transmitted microwave signals comprise different frequencies.

7. The method of claim 1, wherein the received microwave signals each correspond to adjacent pairs of microwave sensors.

8. The method of claim 1, wherein transmitting the microwave signals into the thorax of the patient using the microwave sensors comprises locally coupling the microwave signals into the body without leakage into an adjacent microwave sensor.

9. The method of claim 1, further comprising determining the lung water content using one or more of the received microwave signals.

10. A system for monitoring lung water content of a patient, the system comprising:
    a plurality of microwave sensors; and
    a processor configured to
        cause one or more of the microwave sensors to transmit a plurality of microwave signals into the thorax of a patient;
        receive a plurality of of the microwave signals from one or more of the microwave sensors, the plurality of received microwave signals each comprising at least one frequency component having a magnitude and a phase;
        analyze the phase of the received microwave signal corresponding to a first pair of the microwave sensors to monitor changes in the lung water content; and
        analyze the magnitude of the received microwave signal corresponding to a second, different pair of the microwave sensors to determine whether the change in lung water content indicated by the received microwave signal corresponding to the first pair of microwave sensors is increasing or decreasing.

11. The system of claim 10, wherein the processor is further configured to:
    determine that the lung water content is increasing if the magnitude is decreasing; and
    determine that the lung water content is decreasing if the magnitude is increasing.

12. The system of claim 10, wherein the second pair of microwave sensors is located laterally or posteriorly on the patient's thorax in a viewing area for the lung that is unobstructed by another internal organ.

13. The system of claim 10, wherein the processor is further configured to:
    analyze the received microwave signal corresponding to a pair of the microwave sensors located adjacent to the heart of the patient to determine a blood pressure indicator.

14. The system of claim 13, wherein the processor is further configured to select the received microwave signal corresponding to the second pair of microwave sensors based on correlation with the blood pressure indicator.

15. The system of claim 10, wherein the transmitted microwave signals comprise different frequencies.

16. The system of claim 10, wherein the received microwave signals each correspond to adjacent pairs of microwave sensors.

17. The system of claim 10, wherein the microwave sensors are transmission line-based.

18. The system of claim 10, wherein the processor is further configured to determine the lung water content using one or more of the received microwave signals.

19. The system of claim 10, wherein the microwave sensors in each pair are provided adjacent to one another on a patch.

* * * * *